United States Patent
Uzawa et al.

(10) Patent No.: US 8,164,836 B2
(45) Date of Patent: Apr. 24, 2012

(54) OBJECTIVE LENS FOR ENDOSCOPES

(75) Inventors: Tsutomu Uzawa, Shibuya-Ku (JP);
Hideyasu Takato, Shibuya-Ku (JP)

(73) Assignee: Olympus Medical Systems Corp.,
Tokyo (JP)

( * ) Notice: Subject to any disclaimer, the term of this patent is extended or adjusted under 35 U.S.C. 154(b) by 0 days.

(21) Appl. No.: 12/932,211

(22) Filed: Feb. 16, 2011

(65) Prior Publication Data

US 2011/0235192 A1    Sep. 29, 2011

Related U.S. Application Data

(63) Continuation of application No. PCT/JP2010/003079, filed on Apr. 30, 2010.

(30) Foreign Application Priority Data

May 26, 2009  (JP) ................................. 2009-126037

(51) Int. Cl.
  *G02B 15/14* (2006.01)
  *G02B 21/02* (2006.01)
(52) U.S. Cl. ........................................ 359/690; 359/656
(58) Field of Classification Search .......... 359/656–661, 359/690, 687
See application file for complete search history.

(56) References Cited

U.S. PATENT DOCUMENTS

| | | | | |
|---|---|---|---|---|
| 7,499,226 B2 * | 3/2009 | Takato | ........................... | 359/690 |
| 7,511,892 B2 * | 3/2009 | Takato | ........................... | 359/676 |
| 2010/0142058 A1 * | 6/2010 | Takato | ........................... | 359/661 |

FOREIGN PATENT DOCUMENTS

| | | |
|---|---|---|
| JP | 2001-091832 | 4/2001 |
| JP | 2007-260305 | 10/2007 |

\* cited by examiner

*Primary Examiner* — Jordan Schwartz
(74) *Attorney, Agent, or Firm* — Kenyon & Kenyon LLP

(57) ABSTRACT

The inventive objective lens for endoscopes has independently a zooming function and a focusing function, and is capable of magnified viewing. The objective lens has an angle of view (2ω) of 100° or greater, and comprises a positive first group G1, a negative second group G2 and a positive third group G3. The third group G3 comprises a positive first (3-1) subgroup G31 and a positive second (3-2) subgroup G32. A subgroup in at least the second group G2 moves to (1) bring about a change in the focal length of the whole system and (2) correct an image position for movement in association with a focal length change, and one subgroup in the second group G2 and the third group G3 moves to the image side from a longer side toward a shorter side of the working distance (WD) to (3) correct the focal position for movement in association with a working distance change.

9 Claims, 21 Drawing Sheets

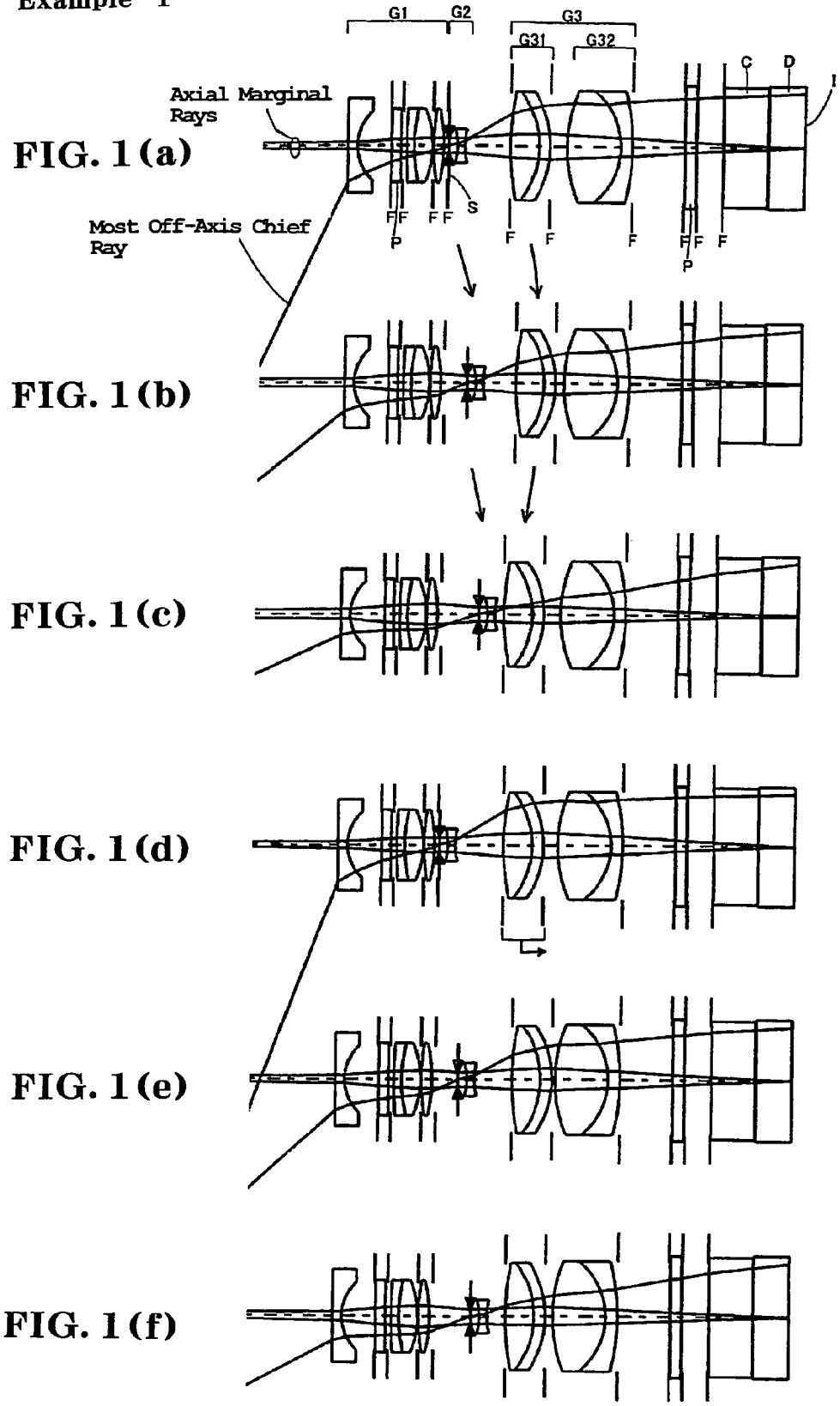

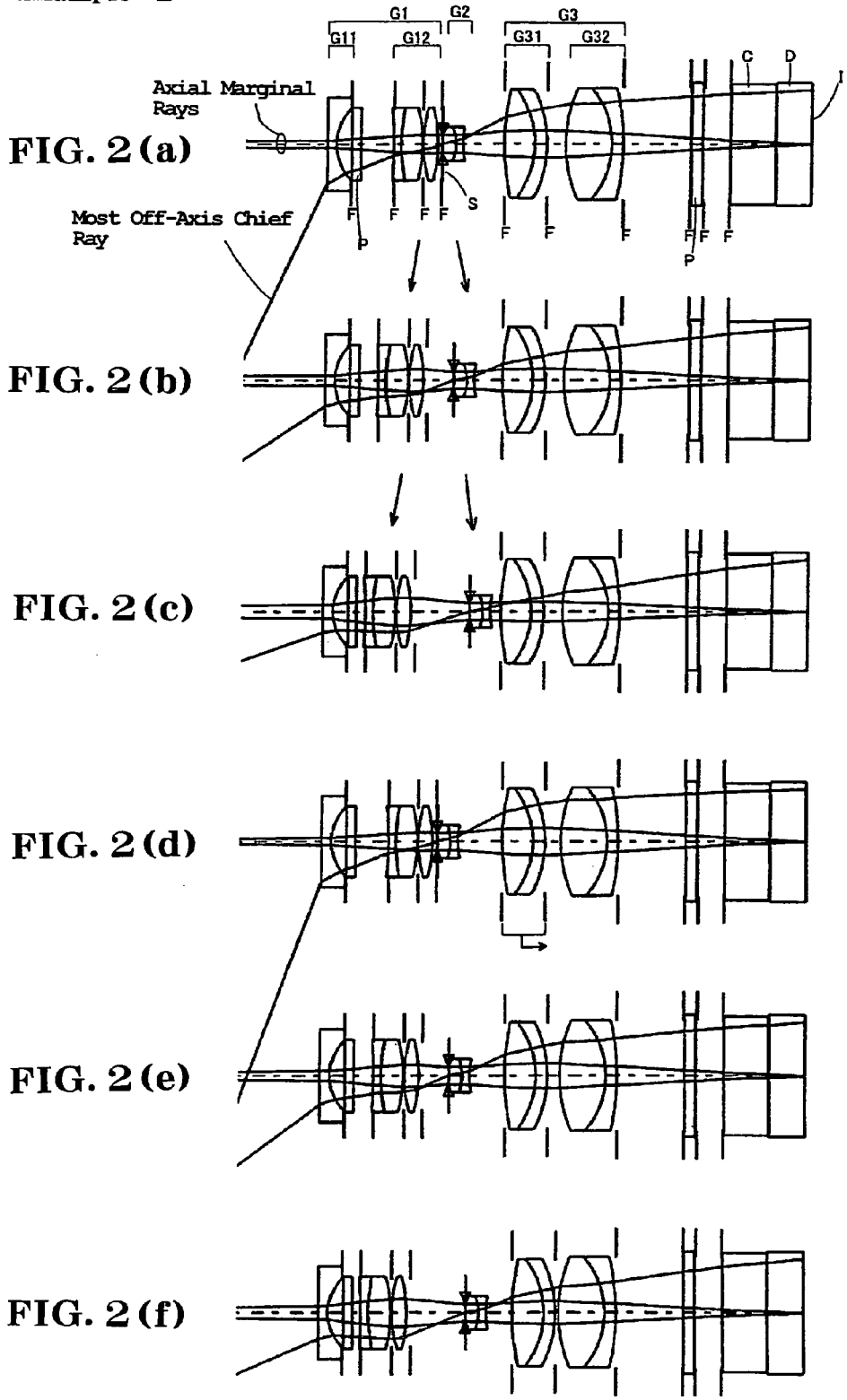

Example 3

Example 4

Example 5

Example 6

Example 7

Example 1

Example 1

435.84 — — —
486.13 —·—·—
656.27 - - - - -
587.56 ————

Example 2

Example 2

435.84
486.13
656.27
587.56

Example 3

Example 3 FIG. 13(a)
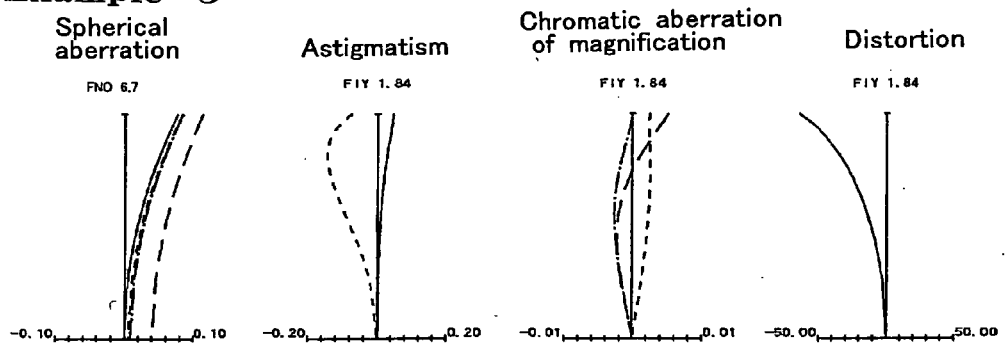
FIG. 13(b)
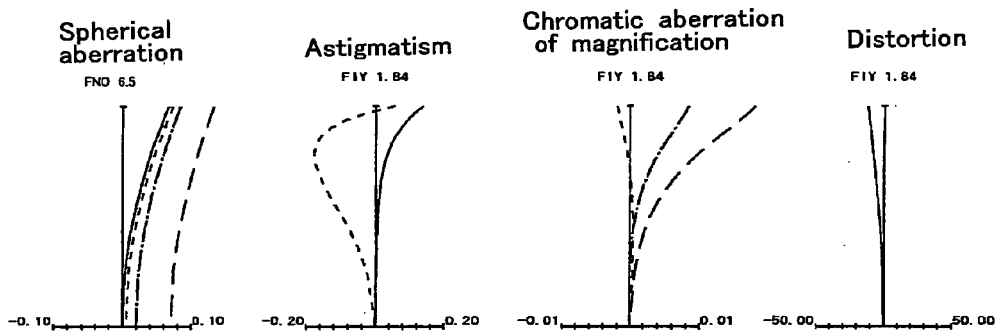
FIG. 13(c)
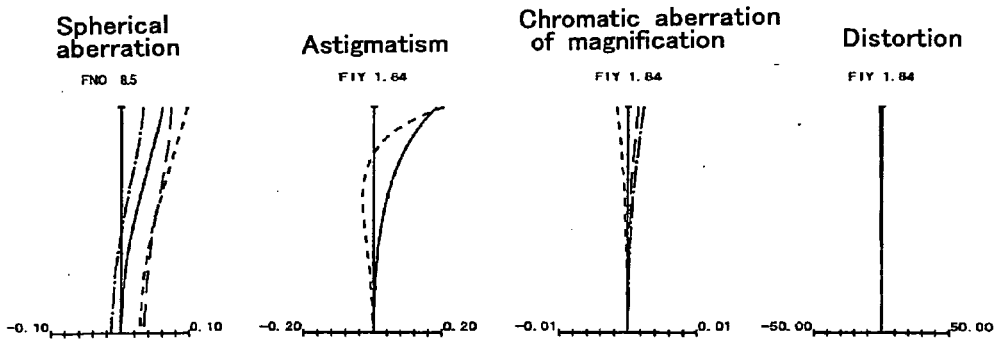
435.84 — — —
486.13 —·—·—
656.27 - - - - -
587.56 ———

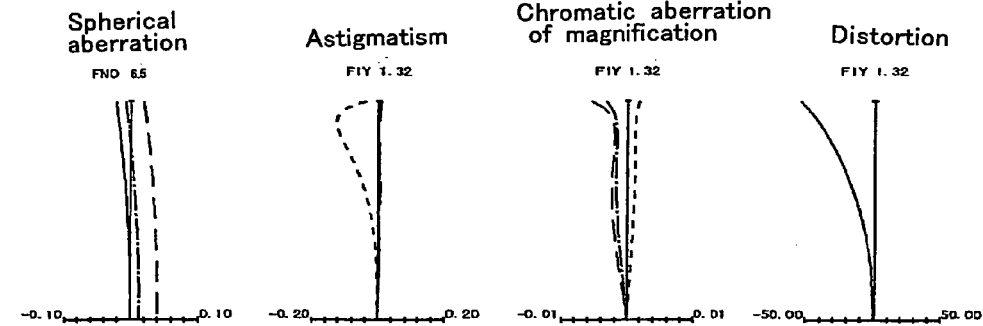
FIG. 14 (a) Example 4
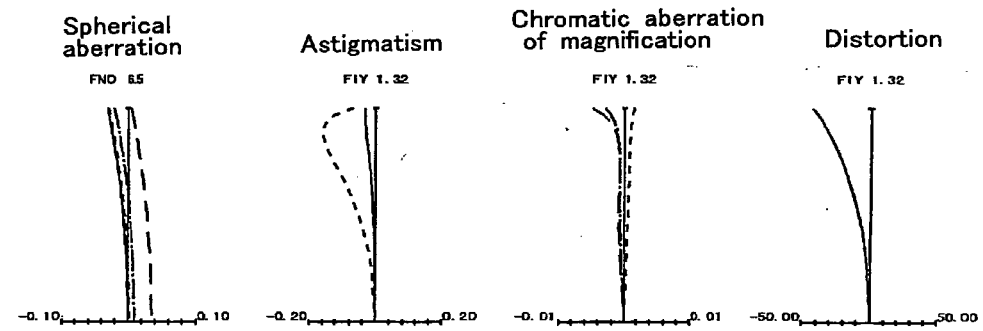
FIG. 14 (b)
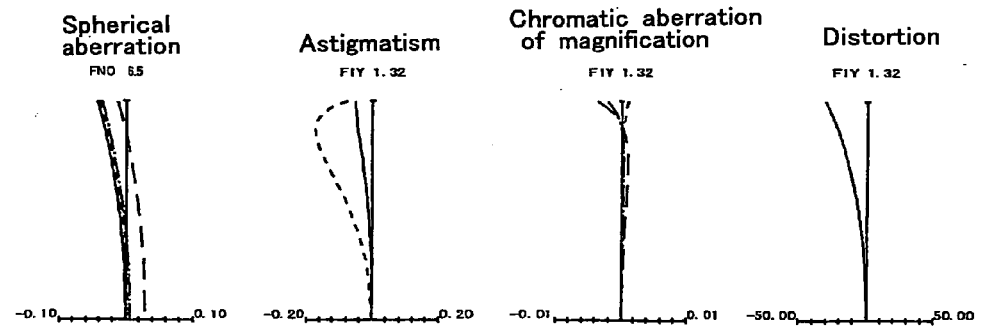
FIG. 14 (c)

Example 4

435.84
486.13
656.27
587.56

Example 5

435.84
486.13
656.27
587.56

Example 5

Example 6

435.84
486.13
656.27
587.56

Example 6

435.84
486.13
656.27
587.56

Example 7

435.84
486.13
656.27
587.56

Example 7

435.84 — — — —
486.13 — · — · —
656.27 — — — — —
587.56 ———

OBJECTIVE LENS FOR ENDOSCOPES

CROSS REFERENCE TO RELATED APPLICATION

This application is a continuation of PCT International Application No. PCT/JP2010/003079 filed on Apr. 30, 2010, which claims priority to Japanese Patent Application No. 2009-126037, filed on May 26, 2009, each of which is expressly incorporated herein in its entirety by reference thereto.

ART FIELD

The present invention relates generally to an objective lens for endoscopes, and more particularly to an objective lens for endoscopes that is capable of ordinary wide-angle viewing as well as magnified viewing.

BACKGROUND ART

Conventional zooming objective lenses used so far on endoscopes embrace the following types.

Type 1

This type is designed to vary magnification with the endoscope body in proximity to the object of interest, and has general applications. One example of implementing proximity magnifications by varying working distances (WD) is set forth in Patent Publication 1.

Type 2

This type is designed to implement zooming in a constant working distance (WD), as set forth typically in Patent Publication 2.

Type 3

This type is designed to implement zooming in a constant working distance and implement proximity magnification while the working distance (WD) is varied, as set forth typically in Patent Publication 3.

In applications other than the endoscopes, on the other hand, video cameras are widely known as equipment having zooming capabilities. A typical example of the objective lens for video cameras is set forth in Patent Publication 4.

Electronic magnification capable of electronically magnifying images is widely known as means without recourse to optical zooming.

LISTING OF THE PATENT PUBLICATIONS

Patent Publication 1: JP(B) 61-44283
Patent Publication 2: JP(A) 2002-14285
Patent Publication 3: JP(A) 58-193512
Patent Publication 4: JP(A) 2000-206407

SUMMARY OF THE INVENTION

Object of the Invention

The terms zooming and focusing here are defined as followed.

By zooming it is intended to vary the focal length of the whole system while keeping a distance from an object to the image plane constant thereby varying imaging magnification; for instance, to vary the magnification while an endoscope remains fixed relative to a subject.

By focusing it is intended to correct a focal position for movement in association with working distance (WD) changes so that it can be kept constant; for instance, to draw an endoscope body near to a subject of interest from where it is in focus on a far subject of interest so that it can be in focus on the near subject of interest.

Means for Accomplishing the Object

According to one preferred embodiment of the invention, there is an objective lens for endoscopes provided, which is characterized by having an angle (2ω) of view of 100° or greater at a wide-angle end, and comprising, in order from an object side thereof, a positive first group, a negative second group and a positive third lens group, wherein:

the third group comprises a positive first (3-1) subgroup and a positive second (3-2) subgroup, a lens subgroup in at least the second group moves to (1) bring about a change in a focal length of a whole system and (2) correct an image position for movement in association with a focal length change, and one subgroup in the second group and the third group moves to an image side from a longer working distance (WD) side toward a shorter working distance side to (3) correct a focal position for movement in association with a working distance change.

The requirements for, and advantages of, the above arrangement are now explained.

For the purpose of achieving an small yet wide-angle-of-view optical system that has a zooming function and a focusing function, a selection of the basic arrangement of the optical system is of vital importance. With the simplest two-group zooming system, there is difficulty offering a sensible tradeoff between the zooming function and size reductions. As the lens groups grow in number, it works more in favor of both zooming and focusing functions, but it would leave the lens arrangement involved more complicated and more undesirable for endoscopes.

The invention has a basic arrangement comprising, in order from its object side, a positive first group, a negative second group and a positive third group, wherein zooming is implemented by movement of two or more subgroups inclusive of at least a lens subgroup in the second group thereby changing the focal length of the whole system and making an image position for movement in association with a focal length change. This in turn makes it possible to change imaging magnification while the working distance is kept constant for magnified viewing. It is here to be noted that the positive and negative attached to the lens group mean that it has positive or negative refracting power. The same will apply hereafter.

Focusing is implemented by moving one subgroup in the second and third groups toward the image side from a longer working distance (WD) side to a shorter working distance side, so that the focal position is corrected for movement in association with a working distance change and the focal position is kept constant. This in turn makes it possible for the endoscope body to draw nearer to, and be in focus on, the subject of interest and, consequently, proximity magnified viewing is achievable.

As a group having a relatively small lens diameter is used as the moving group while the first group remains fixed, it enables the size of the objectives lens involving a mechanical setup to be reduced, and the angle of view (2ω) on the wide-angle side to be set at 100° or greater, a figure being preferable for endoscopes.

Preferably, the second group should have an aperture stop.

As there is the aperture stop positioned at substantially the center of the optical system, it works for keep off-axis ray heights low throughout the optical system. Especially for a wide angle-of-view optical system such as one contemplated herein, it is important to make the lens diameter of the first group small. The location of the aperture stop in the second group is preferable for an endoscope-dedicated optical system, because off-axis ray height through the adjoining first group is kept low. This also enables off-axis ray height to be lowest at the second group so that the lens diameter of the moving group can be made small.

It is also preferable to satisfy the following conditions (1), (2), (3) and (4).

$$0.4<(D12t-D12w)/fw<1.4 \quad (1)$$

$$0.02<\Delta Dwd/fw<0.4 \quad (2)$$

$$0<(rb+ra)/(rb-ra)<2 \quad (3)$$

$$-0.7<1/\beta wd<0.2 \quad (4)$$

Here fw is the focal length of the whole system at the wide-angle end, a figure being obtained in a far end-defining working distance;

D12w is the spacing between the first group and the second group at the wide-angle end;

D12t is the spacing between the first group and the second group at the telephoto end;

ΔDwd is the amount of movement of a moving subgroup upon changing of the working distance from a far end to a near end, provided that a plus sign is indicative of a direction of movement of the moving subgroup toward the image side;

ra is the radius of curvature of the image-side surface of the first lens in the first group;

rb is the radius of curvature of the object-side surface of the second lens in the first group; and βwd is the imaging magnification of the moving group upon a working distance change, a figure being obtained at the wide-angle end in a far end-defining working distance.

Most preferably, all Conditions (1) to (4) should be satisfied. Condition (1) is all about zooming, defining the amount of movement of the group that moves upon zooming.

Being short of the lower limit of 0.4 to Condition (1) would make it impossible to take hold of sufficient zoom ratios by zooming. Exceeding the upper limit of 1.4 may work in favor of making sure zoom ratios; however, it is not preferable for endoscope purposes because the whole lens length grows too long.

Condition (2) is all about focusing, defining the amount of movement of the group that moves upon focusing. Being short of the lower limit of 0.02 to Condition (2) would result in the inability to implement sufficient proximity viewing. Exceeding the upper limit of 0.4 may work in favor of proximity viewing; however, it is not preferable for endoscope purposes because the whole lens length grows too long.

Condition (3) is all about the size reduction of the first group, defining the lens shape at the tip of the lens system.

Exceeding the upper limit of 2 to Condition (3) would not only cause an entrance pupil to go away with the result that the lens diameter of the first group would tend to grow large, but also work against a wide-angle arrangement. Being short of the lower limit of 0 may work for lens diameter reductions; however, it is not preferable because off-axis, higher order aberrations are likely.

Condition (4) is all about focusing, defining the imaging magnification of the group that moves upon focusing.

Deviations from the lower limit of −0.7 or the upper limit of 0.2 to Condition (4), if any, would be less effective for correction of the focal position relative to the amount of movement, with focusing efficiency going worse.

According to a more preferred embodiment of the invention, there is an objective lens for endoscopes provided, which is characterized by having an angle of view (2ω) of 100° or greater at a wide-angle end, and comprising, in order from an object side thereof, a positive first group, a negative second group and a positive third group, wherein:

the second group has an aperture stop, the third group comprises a positive first (3-1) subgroup and a positive second (3-2) subgroup, a lens subgroup in at least the second group moves to (1) bring about a change in a focal length of a whole system and (2) make an image position for movement in association with a focal length change, and one subgroup in the second group and the third group move toward an image side from a longer working distance (WD) side to a shorter working distance side to (3) correct a focal position for movement in association with a working distance change.

A further preferred embodiment of the invention is characterized by satisfying the following Conditions (1) to (4).

$$0.4<(D12t-D12w)/fw<1.4 \quad (1)$$

$$0.02<\Delta Dwd/fw<0.4 \quad (2)$$

$$0<(rb+ra)/(rb-ra)<2 \quad (3)$$

$$-0.7<1/\beta wd<0.2 \quad (4)$$

Here fw is the focal length of the whole system at the wide-angle end, a figure being obtained in a far end-defining working distance;

D12w is the spacing between the first group and the second group at the wide-angle end;

D12t is the spacing between the first group and the second group at the telephoto end;

ΔDwd is the amount of movement of the moving group as the working distance changes from a far end to a near end provided that a plus sign is indicative of a direction of movement of the moving subgroup toward the image side;

ra is the radius of curvature of the image-side surface of the first lens in the first group;

rb is the radius of curvature of the object-side surface of the second lens in the first group; and βwd is the imaging magnification of the moving group at the time of a working distance change, a figure being obtained at the wide-angle end in a far end-defining working distance.

In this embodiment, it is preferable that after ordinary far viewing, near viewing is implemented with the working distance changed from a longer side to a shorter side, and the focal length of the whole system is then changed while the endoscope is kept in a near distance to implement viewing with higher magnifications.

This is one specific application that enables viewing to be implemented in a wider field of view, the subject of interest to be viewed in a near distance on a magnified scale, and viewing to be implemented with higher magnifications while the endoscope is kept in a constant distance. The present invention capable of implementing optical zooming after proximity magnification is less susceptible of image quality deterioration than electronic zooming.

As a matter of course, it is more preferable to add electronic zooming to the present invention.

In a preferable embodiment of the invention:

the second group should move to the image side from the wide-angle side toward the telephoto side;

the first (3-1) subgroup in the third group should move in an orbit distinct from that of the second group in such a way as to correct the image position for movement in association with a focal length change; and the first (3-1) subgroup in the third group should move to the image side from a longer working distance (WD) side toward a shorter working distance side.

This will be embodied in Examples 1 and 7 given later.

This embodiment is simple in that albeit having zooming and focusing functions, there are only two moving groups in all.

It is here to be noted that instead of moving the first (3-1) subgroup in the third group to the image side from a longer working distance (WD) to a shorter working distance side, it is also possible to move the second (3-2) subgroup to the object side. However, the second (3-2) subgroup is less favorable for movement because of its relatively large size.

Most preferably, the aperture stop should be located in the second group.

In a preferable embodiment of the invention:

the first group should comprise a negative first (1-1) subgroup and a positive second (1-2) subgroup;

the second group should move to the object side from the wide-angle side to the telephoto side;

the second (1-2) subgroup in the first group should move in an orbit distinct from that of the second group in such a way as to correct the image position for movement in association with a focal length change; and the first (3-1) subgroup in the third group should move to the image side from a longer working distance (WD) side toward a shorter working distance side.

This will be embodied in Example 2 given later.

This embodiment enables the mechanical arrangement and control system involved to be simplified because the zooming and focusing functions are shared by separate groups.

In a preferable embodiment of the invention:

the first group should comprise a negative first (1-1) subgroup and a positive second (1-2) subgroup;

from the wide-angle side to the telephoto side, the second (1-2) subgroup should move to the object side and the second group should move to the image side;

the first (3-1) subgroup in the third group should move in an orbit distinct from those of the second (1-2) subgroup and the second group in such a way as to correct the image position for movement in association with a focal length change; and the first (3-1) subgroup in the third group should move to the image side from a longer working distance (WD) side toward a shorter working distance side.

This will be embodied in Example 3 given later.

This embodiment works in favor of higher zoom ratios because the zooming function is shared by three groups. Most preferably, the aperture stop should be located in the second group.

In a preferable embodiment of the invention:

the first group should comprise a negative first (1-1) subgroup) and a positive second (1-2) subgroup;

the second (1-2) subgroup should move to the object side from the wide-angle side to the telephoto side;

the second group should move in an orbit distinct from that of the second (1-1) subgroup in such a way as to correct the image position for movement in association with a focal length change; and the second group should move to the image side from a longer working distance (WD) side toward a shorter working distance side.

This will be embodied in Example 4 given later.

This embodiment is simple in that albeit having zooming and focusing functions, there are only two moving groups in all. Most preferably, the aperture stop should be located in the second group.

In a preferable embodiment of the invention, the second group should comprise a negative first (2-1) subgroup and a negative second (2-2) subgroup;

from the wide-angle side to the telephoto end, the first (2-1) subgroup should move to the object side and the second (2-2) subgroup should move to the image side;

the third group should move in an orbit distinct from those of the first (2-1) and second (2-2) subgroups in the second group in such a way as to correct the image position for movement in association with a focal length change; and the second (2-2) subgroup in the second group should move to the image side from a longer working distance (WD) side toward a shorter working distance side (see Claims 1, 2 and 4).

This will be embodied in Example 5 given later.

In this embodiment, the second (2-2) subgroup in the second group is small enough to work in favor of movement. Most preferably the aperture stop should be located in the second group.

In a preferred embodiment of the invention:

the second group should comprise a positive first (2-1) subgroup and a negative second (2-2) subgroup;

the second (2-2) subgroup should move to the image side from the wide-angle side to the telephoto side;

the first (2-1) subgroup should move in an orbit distinct from that of the second (2-2) subgroup in such a way as to correct the image position for movement in association with a focal length change; and the second (2-2) subgroup should move to the image side from a longer working distance (WD) side toward a shorter working distance side.

This will be embodied in Example 6 given later.

This embodiment is simple in that albeit having zooming and focusing functions, there are only two moving groups in all. Making the smallest group movable is favorable for reducing the size of the objective lens inclusive of mechanical arrangements. Most preferably, the aperture stop should be located in the second group.

Advantages of the Invention

According to the present invention, there is an objective lens suitable for use on endoscopes, which has independently a zooming function and a focusing function, and is capable of magnified viewing.

BRIEF EXPLANATION OF THE DRAWINGS

FIG. 1 is illustrative in lens section of the objective lens for endoscopes according to inventive Example 1 as viewed in distinct working distances at the wide-angle end, in the intermediate setting, and at the telephoto end.

FIG. 2 is illustrative in lens section, as in FIG. 1, of the objective lens for endoscopes according to inventive Example 2.

FIG. 13 is similar aberration diagrams for Example 3 as in FIG. 9.

FIG. 14 is indicative of spherical aberrations, astigmatisms, chromatic aberrations of magnification and distortions of Example 4 as found in the states of FIGS. 4(a) to 4(c).

EMBODIMENTS FOR CARRYING OUT THE INVENTION

Figures 3A, 3B, 3C, 3D, 3E, 3F:
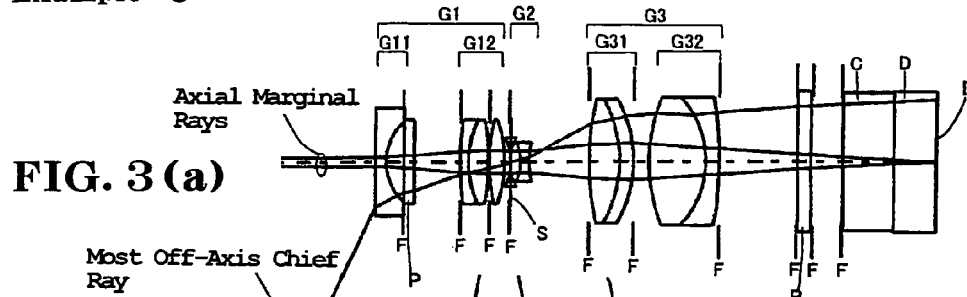
FIG. 3 is illustrative in lens section, as in FIG. 1, of the objective lens for endoscopes according to inventive Example 3.

Inventive Examples 1 to 7 of the objective lens for endoscopes according to the invention are now explained.

FIG. 1 is illustrative in lens section of the objective lens for endoscopes according to Example 1 as viewed at the wide-angle ends (a) and (d), in the intermediate settings (b) and (3) and at the telephoto ends (c) and (f) when its working distances are at the far ends (a) to (c) and at the near ends (d) to (f). In this objective lens, the first, second and third groups are indicated by G1, G2 and G3, respectively, and the first and second subgroups in the third group G3 are indicated by G31 and G32, respectively. The aperture stop and image plane are indicated by S and I, respectively. In FIG. 1, the capital P stands for an optical member that may be a laser cut filter, an infrared cut filter, an optical low-pass filter; C a cover glass; D a CCD chip sealing glass; and F a flare stop. The action arrows bridging the gaps between FIGS. 1(a) and 1(b) and between the FIGS. 1(b) and 1(c) roughly stand for the direction of movement of the lens groups, and the action arrow in FIG. 1(d) stands for the direction of movement of the lens groups when the working distance is changed from the far end to the near end. In FIGS. 1(a) to 1(c), it is noted that for simplification of illustrations, these symbols are indicated in FIG. 1(a) only, but they are not given in other drawings. Further, the surface numbers of optical surfaces and surface separations are also left out for the same reason. It is noted that the same symbols, action arrows and illustrations as described above will apply to Examples 2 to 7 (FIGS. 2 to 7) too.

Numeral data on Examples 1 to 7 will be given later. Referring to the surface number, however, the surface number of an optical surface as counted from the tip surface in the first group G1 is indicated by No; the radius of curvature by r; the surface separation or air spacing by d; the d-line refractive index by nd; and the Abbe constant by νd, respectively. The radius of curvature, surface separations and focal length are given in mm.

As shown in FIG. 1, the objective lens for endoscopes according to Example 1 are built up of the positive first group G1 made up of a plano-concave negative lens, a cemented lens of a negative meniscus lens convex on its object side and a double-convex positive lens, and a double-convex positive lens, the negative second group G2 having the aperture stop S located integrally on its object side and made up of a cemented lens of a positive meniscus lens concave on its object side and a double-concave negative lens, and the positive third group G3 made up of a cemented lens of a double-convex positive lens and a negative meniscus lens concave on its object side and a cemented lens a double-convex position lens and a negative meniscus lens concave on its object side. Here the object-side cemented lens in the third group G3 defines the positive first subgroup G31, and the image-side cemented lens defines the positive second subgroups G32. The optical members P such as laser cut filters are provided, one located between the plano-concave negative lens and the cemented lens in the first group G1, and another located on the image side of the third group G3. To the image side of the image-side optical member in the third group G3, the cover glass C and CCD chip sealing glass D are joined, and the image plane I is positioned behind the CCD chip sealing glass D. The planes indicated by Surface Nos. 3, 6, 10, 13, 18, 22, 26, 27, 30 and 31 in the numeral data given later represent flare stops F.

FIG. 1(a) illustrates the objective lens at the wide-angle end and at a far end defined by a working distance of 30 mm; FIG. 1(b) illustrate the objective lens in the intermediate setting and at the far end defined by the same working distance; FIG. 1(c) illustrates the objective lens at the telephoto end and at the far end defined the same working distance; FIG. 1(d) illustrates the objective lens at the wide-angle end and at a near end defined by a working distance 15 mm; FIG. 1(e) illustrates the objective lens in the intermediate setting and at the near end defined by the same working distance; and FIG. 1(f) illustrates the objective lens at the telephoto end and at the near end defined by the same working distance. At the far end the first group G1 and the second subgroup G32 in the third group G3 remains fixed from the wide-angle end to the telephoto end. Meanwhile, the second group G2 moves monotonously to the image side, and the first subgroup G31 in the third group G3 moves to the image side as far as the intermediate setting with a decreasing spacing between it and the second group G2, and then moves to the object side from the intermediate setting to the telephoto end, taking the same position at both the wide-angle end and at the far end.

At the time of changing the working distance from the far end to the near end, the first subgroup G31 in the third group G3 moves to the image side in the respective states of FIGS. 1(a) to 1(c). More specifically, at the near end the second group G2 moves monotonously to the image side from the wide-angle end to the telephoto end as is the case with the far end, and the first subgroup G31 in the third group G3 moves in an orbit nearer to the image side than that at the far end, as is not the case with the far end: that first subgroup G31 moves to the image side as far as the intermediate setting with a decreasing spacing between it and the second group G2, and then moves to the object side from the intermediate setting to the telephoto end, taking a position nearer to the image side at the telephoto end than at the wide-angle end.

Figure 8A:
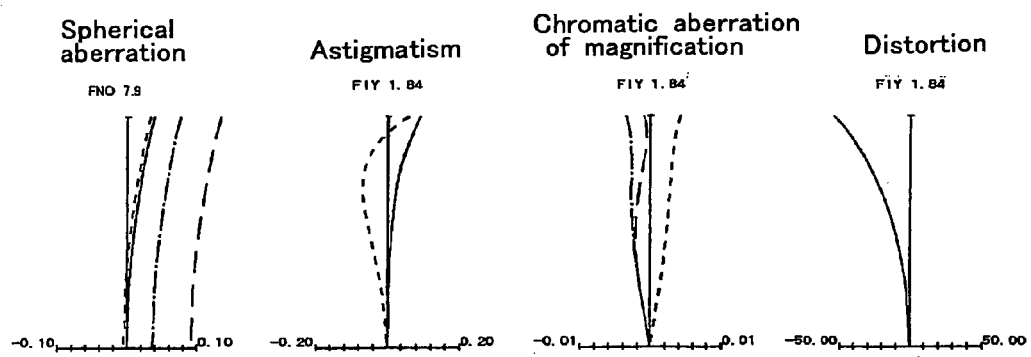
FIG. 8 is indicative of spherical aberrations, astigmatisms, chromatic aberrations of magnification and distortions of Example 1 as found in the states of FIGS. 1(a) to 1(c).
Figure 8B:
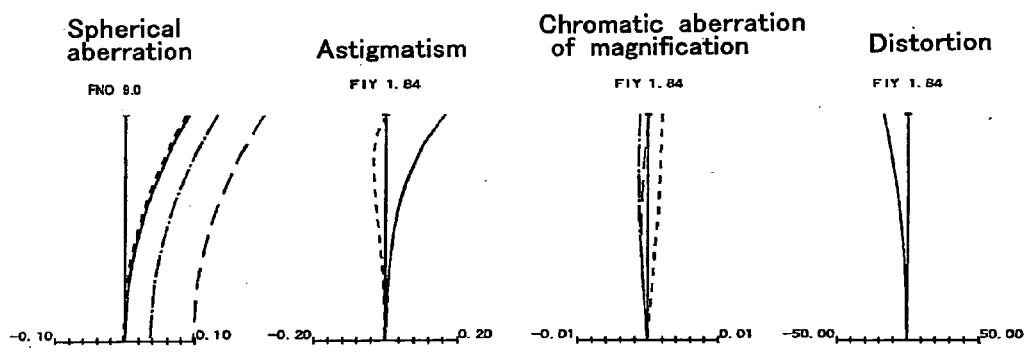
Figure 8C:
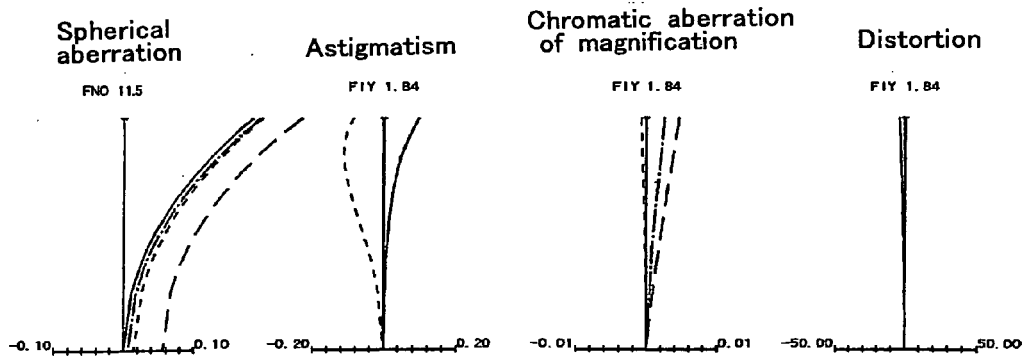
Figure 9:
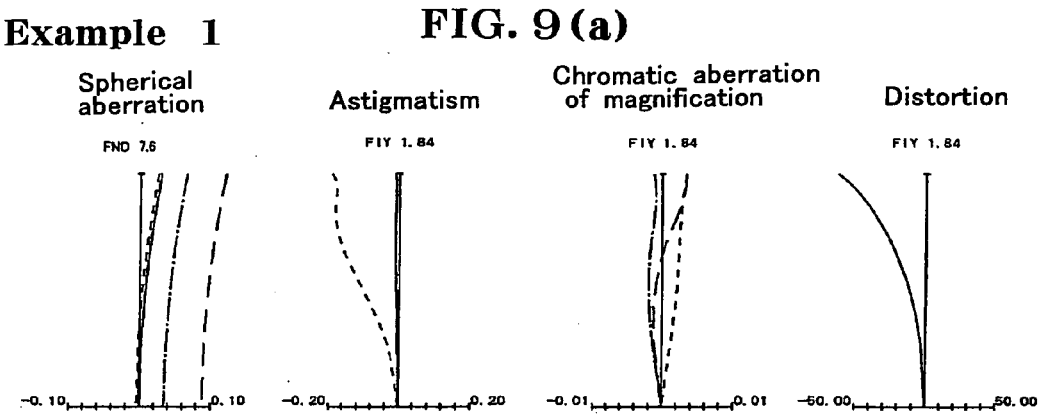
FIG. 9 is indicative of spherical aberrations, astigmatisms, chromatic aberrations of magnification and distortions of Example 1 as found in the states of FIGS. 1(d) to 1(f).
Figure 9:
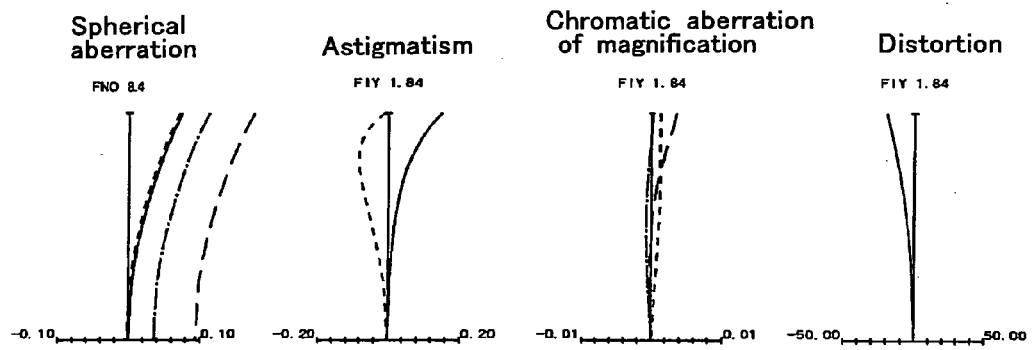
Figure 9:
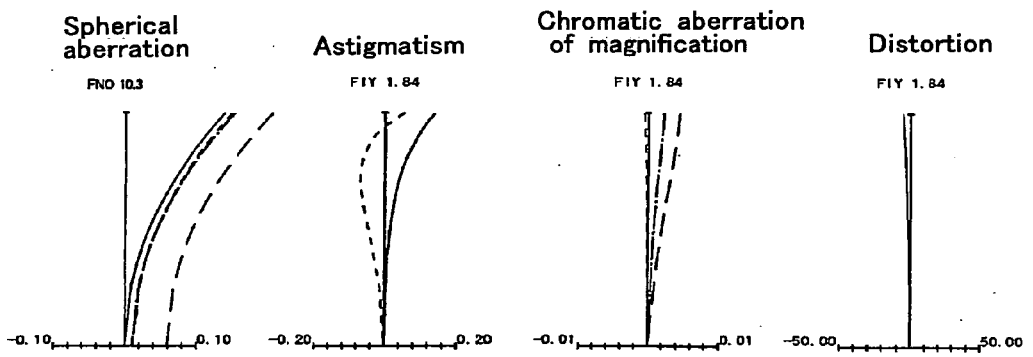

Aberration curve diagrams for Example 1 in the states of FIGS. 1(a), 1(b) and 1(c) are attached hereto as FIGS. 8(a), 8(b) and 8(c), and those in the states of FIGS. 1(d), 1(e) and 1(f) are attached hereto as FIGS. 9(a), 9(b) and 9(c). The aberration curve diagrams are presented with the amounts (mm) of aberrations except distortion as abscissa, and the amount (%) of distortion is shown as abscissa. FIY means the image height (mm), and the wavelengths of aberration curves are given in nm. The same will apply hereafter.

FIG. 2 is illustrative in lens section, as in FIG. 1, of the objective lens for endoscopes according to Example 2. The first, second and third groups of this objective lens are indicated by G1, G2 and G3, respectively; the first and second subgroups in the first group G1 are indicated by G11 and G12, respectively; and the first and second subgroups in the third group G3 are indicated by G31 and G32, respectively.

As shown in FIG. 2, the objective lens for endoscopes according to Example 2 is built up of the positive first group G1 made up of a plano-concave negative lens, a cemented lens of a double-concave negative lens and a double-convex positive lens and a double-convex positive lens, the negative second group G2 having the aperture stop S located integrally on its object side and made up of a cemented lens of a positive meniscus lens concave on its object side and a double-concave negative lens, and the positive third group G3 made up of a cemented lens of a double-convex positive lens and a negative meniscus lens concave on its object side and a cemented lens of a double-convex positive lens and a negative meniscus lens concave on its object side. The plano-concave negative lens in the first group G1 defines the negative first subgroup G11; the cemented lens and double-convex positive lens in the first group G1 define the positive second subgroup G12; the object-side cemented lens in the third group G3 defines the positive first subgroup G31; and the image-side cemented lens in the third group G3 defines the positive second subgroup G32. The optical members P such as laser cut filters are provided, one located between the plano-concave negative lens and the cemented lens in the first group G1, and another located on the image side of the third group G3. To the image side of the image-side optical member in the third group G3, the cover glass C and CCD chip sealing glass D are joined, and the image plane I is positioned behind the CCD chip sealing glass D. The planes indicated by Surface Nos. 3, 6, 10, 13, 18, 22, 26, 27, 30 and 31 in the numeral data given later represent flare stops F.

FIG. 2(a) illustrates the objective lens at the wide-angle end and at a far end defined by a working distance of 30 mm; FIG. 2(b) illustrate the objective lens in the intermediate setting and at the far end defined by the same working distance; FIG. 2(c) illustrates the objective lens at the telephoto end and at the far end defined by the same working distance; FIG. 2(d) illustrates the objective lens at the wide-angle end and at a near end defined by a working distance of 15 mm; FIG. 2(e) illustrates the objective lens in the intermediate setting and at the near end defined by the same working distance; and FIG. 2(f) illustrates the objective lens at the telephoto end and at the near end defined by the same working distance. At the far end the first subgroup G11 in the first group G1 and the third group G3 remain fixed from the wide-angle end to the telephoto end. Meanwhile, the first subgroup G12 in the first group G1 moves monotonously to the object side and the second group G2 moves monotonously to the image side.

At the time of changing the working distance from the far end to the near end, the first subgroup G31 in the third group G3 moves to the image side in the respective states of FIGS. 2(a) to 2(c).

Figure 10:
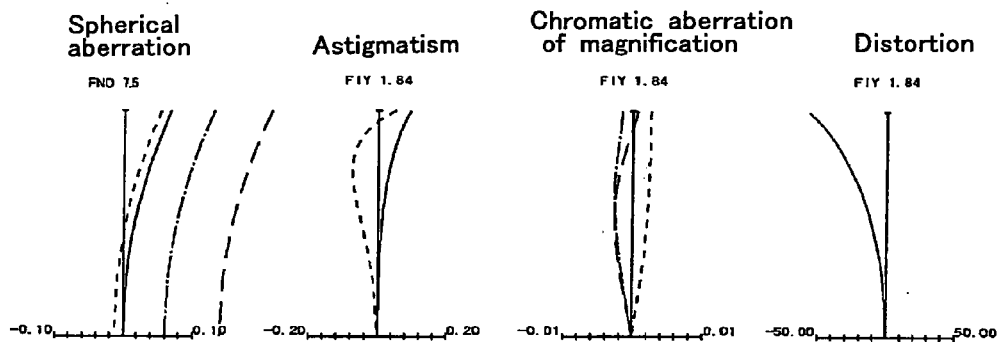
FIG. 10 is similar aberration diagrams for Example 2 as in FIG. 8.
Figure 10:
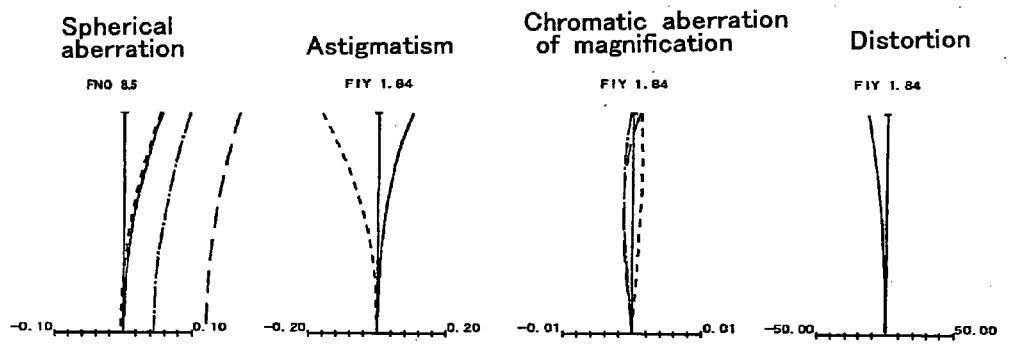
Figure 10:
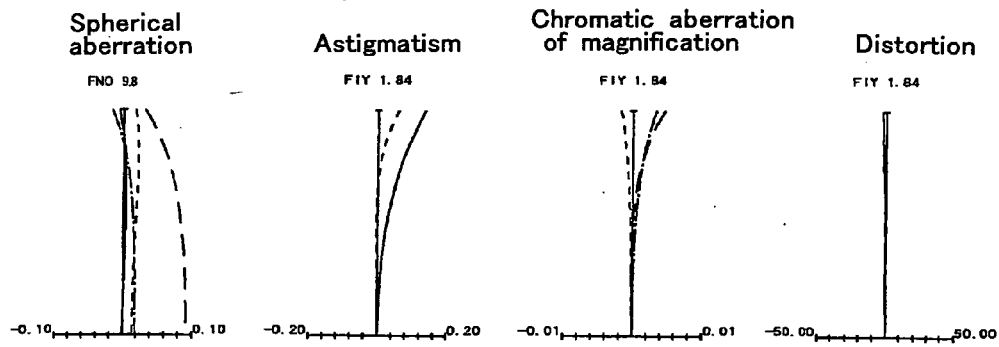
Figure 11:
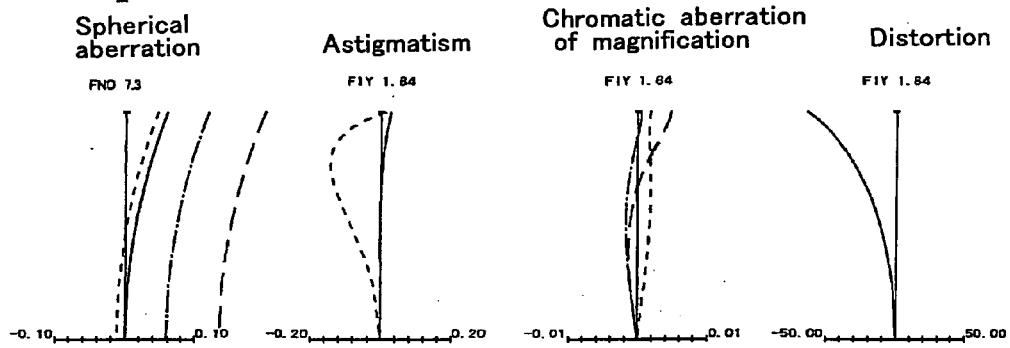
FIG. 11 is similar aberration diagrams for Example 2 as in FIG. 9.
Figure 11:
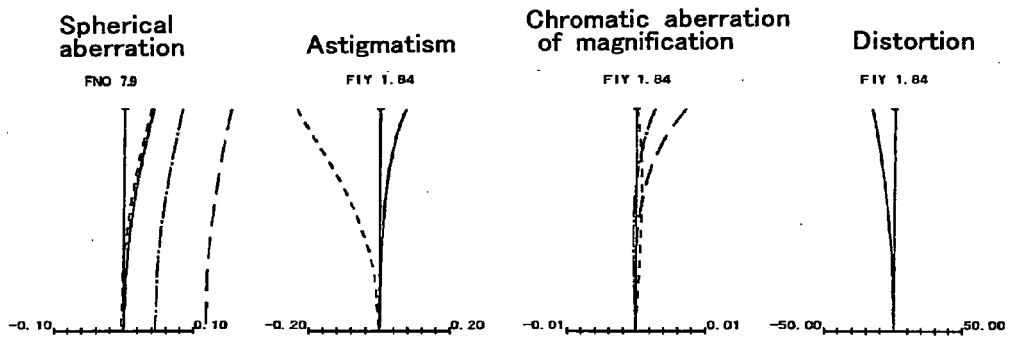
Figure 11:
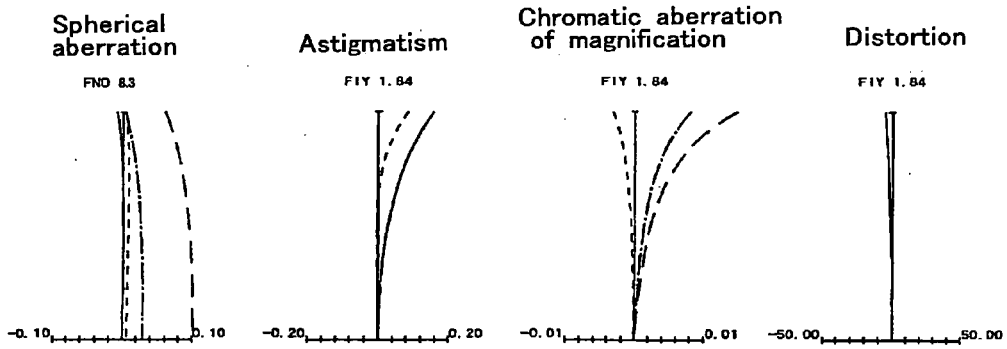

Aberration curve diagrams for Example 2 in the states of FIGS. 2(a), 2(b) and 2(c) are attached hereto as FIGS. 10(a), 10(b) and 10(c), and those in the states of FIGS. 2(d), 2(e) and 2(f) are attached hereto as FIGS. 11(a), 11(b) and 11(c).

FIG. 3 is illustrative in lens section, as in FIG. 1, of the objective lens for endoscopes according to Example 3. The first, second and third groups of this objective lens are indicated by G1, G2 and G3, respectively; the first and second subgroups in the first group G1 are indicated by G11 and G12, respectively; and the first and second subgroups in the third group G3 are indicated by G31 and G32, respectively.

As shown in FIG. 3, the objective lens for endoscopes according to Example 3 is built up of the positive first group G1 made up of a plano-concave negative lens, a cemented lens of a negative meniscus lens convex on its object side and a double-convex positive lens, and a double-convex positive lens, the negative second group G2 having the aperture stop S located integrally on its object side and made up of a cemented lens of a positive meniscus lens concave on its object side and a double-concave negative lens, and the positive third group G3 made up of a cemented lens of a double-convex positive lens and a negative meniscus lens concave on its object side and a cemented lens of a double-convex positive lens and a negative meniscus lens concave on its object side. The plano-concave negative lens in the first group G1 defines the negative first subgroup G11; the cemented lens and double-convex positive lens in the first group G1 define the positive second subgroup G12; the object-side cemented lens in the third group G3 defines the positive first subgroup G31; and the image-side cemented lens in the third group G3 defines the positive second subgroup G32. The optical members P such as laser cut filters are provided, one located between the plano-concave negative lens and the cemented lens in the first group G1, and another located on the image side of the third group G3. To the image side of the image-side optical member in the third group G3, the cover glass C and CCD chip sealing glass D are joined, and the image plane I is positioned behind the CCD chip sealing glass D. The planes indicated by Surface Nos. 3, 6, 10, 13, 18, 22, 26, 27, 30 and 31 in the numeral data given later represent flare stops F.

FIG. 3(a) illustrates the objective lens at the wide-angle end and at a far end defined by a working distance of 30 mm; FIG. 3(b) illustrates the objective lens in the intermediate setting and at the far end defined by the same working distance; FIG. 3(c) illustrates the objective lens at the telephoto end and at the far end defined by the same working distance; FIG. 3(d) illustrates the objective lens at the wide-angle end and at a near end defined by a working distance of 15 mm; FIG. 3(e) illustrates the objective lens in the intermediate setting and at the near end having the same working distance; and FIG. 3(f) illustrates the objective lens at the telephoto end and at the near end defined by the same working distance. At the far end the first subgroup G11 in the first group G1 and the second subgroup G32 in the third group G3 remain fixed from the wide-angle end to the telephoto end. Meanwhile, the second subgroup G12 in the first group G1 moves monotonously to the object side and the second group G2 moves monotonously to the image side, and the first subgroup G31 in the third group G3 moves to the image side as far as the intermediate setting with a decreasing spacing between it and the second group G2, and then moves to the object side from the intermediate setting to the telephoto end with a decreasing spacing between it and the second group G2, taking a position nearer to the object side at the telephoto end than at the wide-angle end.

At the time of changing the working distance from the far end to the near end, the first subgroup G31 in the third group G3 moves to the image side in the respective states of FIGS. 3(a) to 3(c). More specifically, at the near end the second subgroup G12 in the first group G1 and the second group G2 move monotonously to the image side from the wide-angle end to the telephoto end as is the case with the far end, and the first subgroup G31 in the third group G3 moves in an orbit nearer to the image side than that at the far end, as is not the case with the far end: that first subgroup G31 moves to the image side as far as the intermediate setting with a decreasing spacing between it and the second group G2, and then moves to the object side from the intermediate setting to the telephoto end, taking a position slightly nearer to the image side at the telephoto end than at the wide-angle end.

Figure 12:
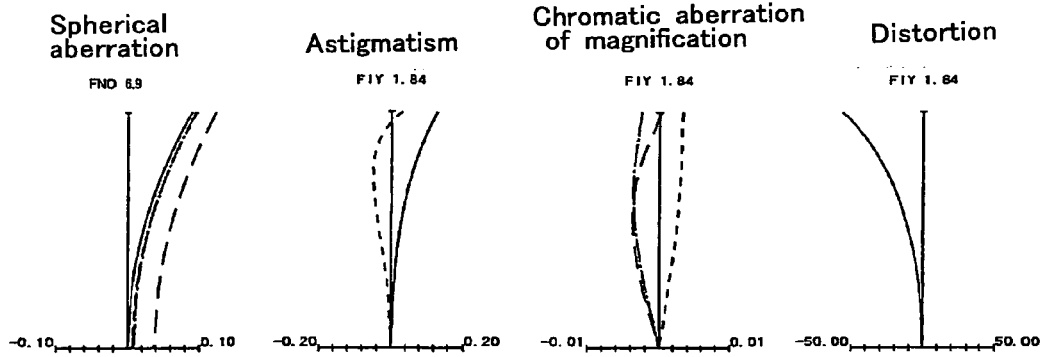
FIG. 12 is similar aberration diagrams for Example 3 as in FIG. 8.
Figure 12:
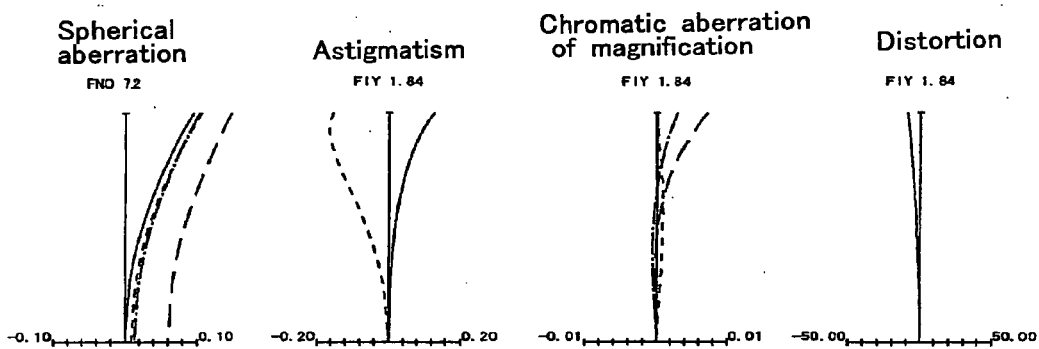
Figure 12:
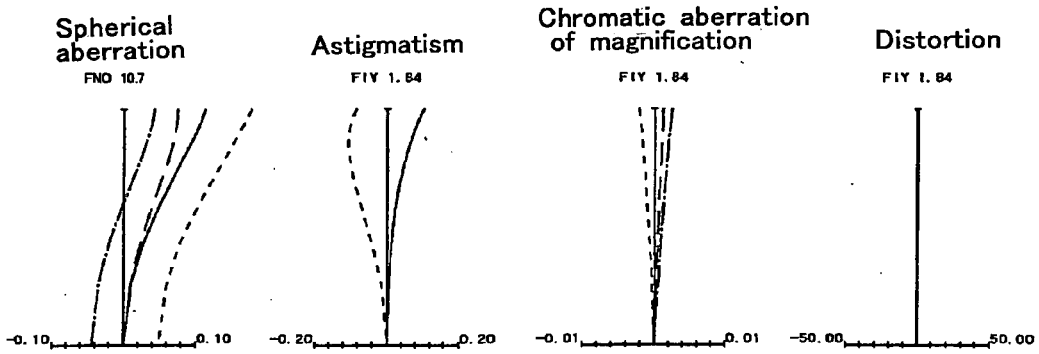

Aberration curve diagrams for Example 3 in the states of FIGS. 3(a), 3(b) and 3(c) are attached hereto as FIGS. 12(a), 12(b) and 12(c), and those in the states of FIGS. 3(d), 3(e) and 3(f) are attached hereto as FIGS. 13(a), 13(b) and 13(c).

Figure 4A:
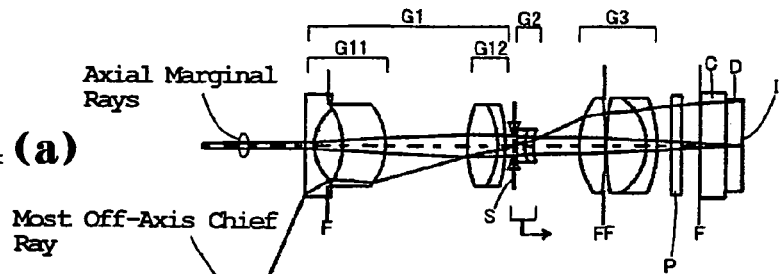
FIG. 4 is illustrative in lens section of the objective lens for endoscopes according to inventive Example 4 as viewed in varied working distances at the wide-angle end, and at the wide-angle end, in the intermediate setting, and at the telephoto end at a near end.
Figure 4B:
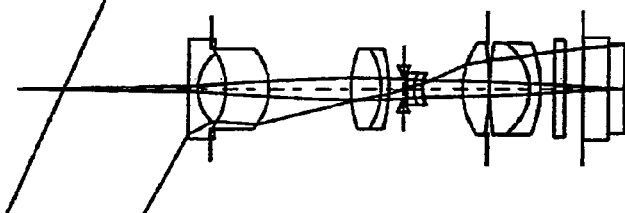
Figure 4C:
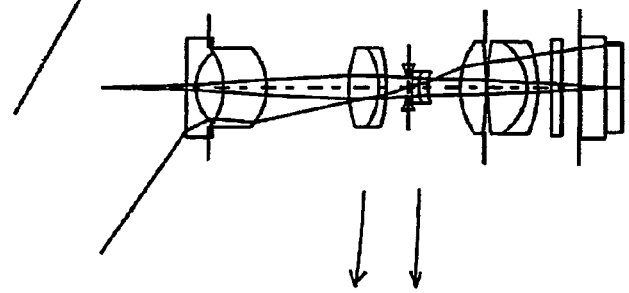
Figure 4D:
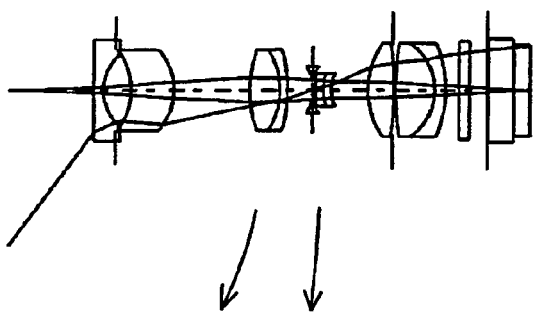
Figure 4E:
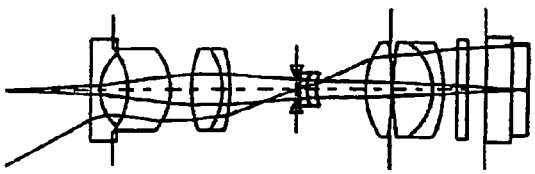

FIGS. 4(a), 4(b) and 4(c) are illustrative in lens section and at the wide-angle end of the objective lens for endoscopes according to Example 4 at the time when it is working at an far end, in an intermediate distance and at a near end, and FIGS. 4(d), 4(e) and 4(f) are illustrative in lens section in the intermediate setting and at telephoto end of the objective lens at the time when it is working at a near end. The first, second and third groups of this objective lens are indicated by G1, G2 and G3, respectively, and the first and second subgroups in the first group are indicated by G11 and G12, respectively.

As shown in FIG. 4, the objective lens for endoscopes according to Example 4 is built up of the positive first group G1 made up of a plano-concave negative lens, a positive meniscus lens concave on its object side and a cemented lens of a double-convex positive lens and a negative meniscus lens concave on its object side, the negative second group G2 having the aperture stop S located integrally on its object side and made up of a cemented lens of a negative meniscus lens convex on its object side and a positive meniscus lens convex on its object side, and the positive third group G3 made up of a double-convex positive lens and a cemented lens of a double-convex positive lens and a negative meniscus lens concave on its object side. The plano-concave negative lens and positive meniscus lens in the first group G1 define the negative first subgroup G11, and the cemented lens defines the positive second subgroup G12. The optical member P such as a laser cut filters is located on the image side of the third group G3. To the image side of the image-side optical member in the third group G3, the cover glass C and CCD chip sealing glass D are joined, and the image plane I is positioned behind the CCD chip sealing glass D. The planes indicated by Surface Nos. 3, 15, 16 and 22 in the numeral data given later represent flare stops F.

FIG. 4(a) illustrates the objective lens at the wide-angle end and at a far end defined by a working distance of 15 mm; FIG. 4(b) illustrates the objective lens in the intermediate setting and at a far end defined by a working distance of 5 mm; FIG. 4(c) illustrates the objective lens at the wide-angle end and at a near end defined by a working distance of 2.47641 mm; FIG. 4(d) illustrates the objective lens in the intermediate setting and at a near end having a working distance of 2.47641 mm; and FIG. 4(e) illustrates the objective lens at the telephoto end and at a near end defined by a working distance of 2.47641 mm. At the far end the first subgroup G11 in the first group G1 and the third group G3 remain fixed from the wide-angle end to the telephoto end. Meanwhile, the second subgroup G12 in the first group G1 moves monotonously to the object side and the second group G2 moves monotonously to the object side with an increasing spacing between it and the second subgroup G12 (FIGS. 4(c) to 4(e)).

Upon changing the working distance at the wide-angle end from the far end to the near end, the second group G2 moves to the image side (FIGS. 4(a) to 4(c)).

Figure 15:
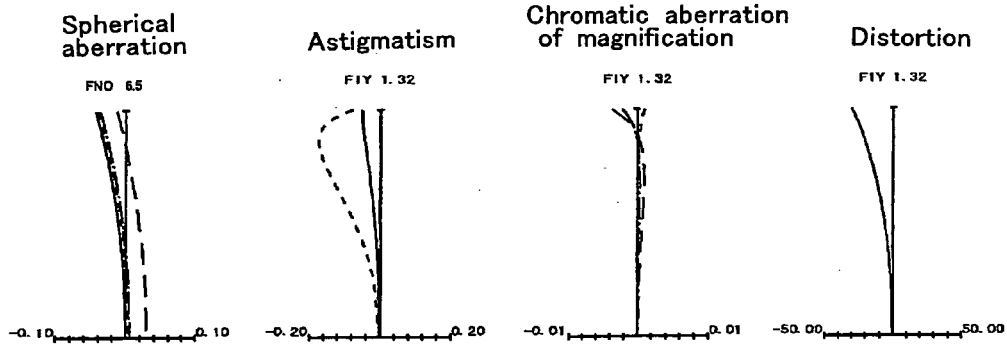
FIG. 15 is indicative of spherical aberrations, astigmatisms, chromatic aberrations magnification and distortions of Example 4 as found in the states of FIGS. 4(c) to 4(e).
Figure 15:
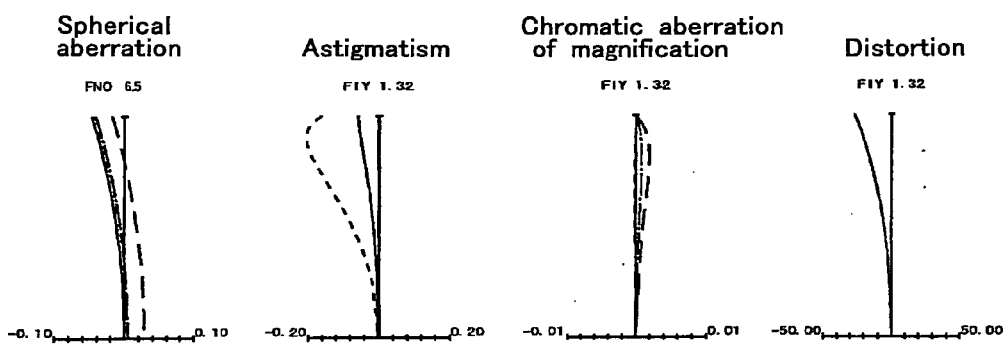
Figure 15:
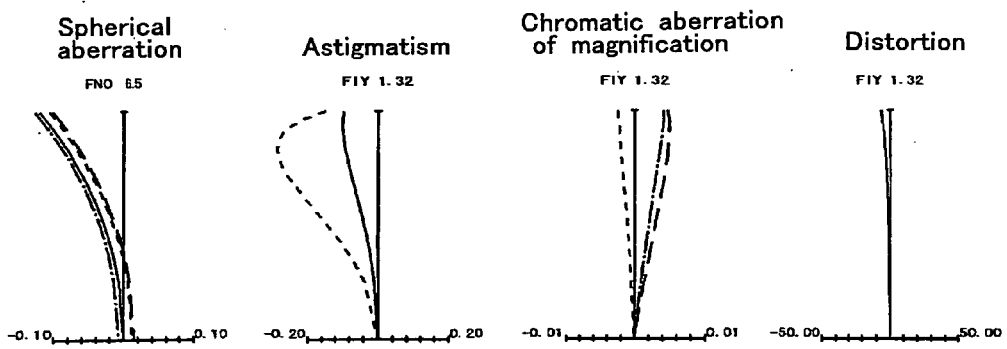

Aberration curve diagrams for Example 4 in the states of FIGS. 4(a), 4(b) and 4(c) are attached hereto as FIGS. 14(a), 14(b) and 14(c), and those in the states of FIGS. 4(c), 4(d) and 4(e) are attached hereto as FIGS. 15(a), 15(b) and 15(c).

FIG. 5 is illustrative in lens section, as in FIG. 4, of the objective lens for endoscopes according to Example 5. The first, second and third groups of this objective lens are indicated by G1, G2 and G3, respectively, and the first and second subgroups in the second group G2 are indicated by G21 and G22, respectively.

As shown in FIG. 5, the objective lens for endoscopes according to Example 5 is built up of the positive first group G1 made up of a plano-concave negative lens, a positive meniscus lens concave on its object side and a cemented lens of a double-convex positive lens and a negative meniscus lens concave on its object side, the negative second group G2 having the aperture stop S located on its object side and made up of a negative meniscus lens concave on its object side and a cemented lens of a negative meniscus lens convex on its object side and a negative meniscus lens convex on its object side and the positive third group G3 made up of a double-convex positive lens and a cemented lens of a positive meniscus lens concave on its object side and a negative meniscus lens concave on its object side. The single negative meniscus lens in the second group G2 defines the negative first subgroup G21 and the cemented lens defines the negative second subgroup G22. The aperture stop S is integrally located on the object side of the single negative meniscus lens. The optical member P such as a laser cut filter is located on the image side of the third group G3. To the image-side optical member P in the third group G3, the cover glass C and CCD chip sealing glass D are joined, and the image plane I is positioned behind the CCD chip sealing glass D. The planes indicated by Surface Nos. 3, 4, 5, 19, 20 and 26 in the numeral data given later are flare stops F.

Figure 5A:
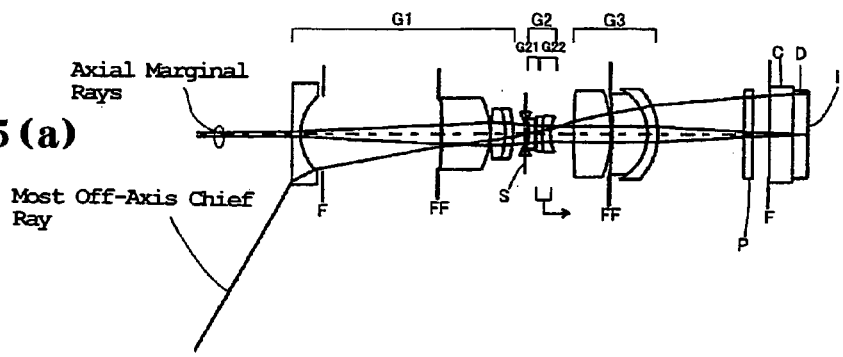
FIG. 5 is illustrative in lens section, as in FIG. 1, of the objective lens for endoscopes according to inventive Example 5.
Figure 5B:
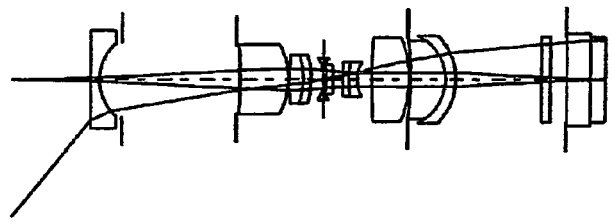
Figure 5C:
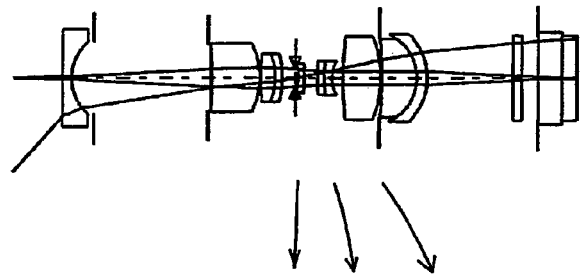
Figure 5D:
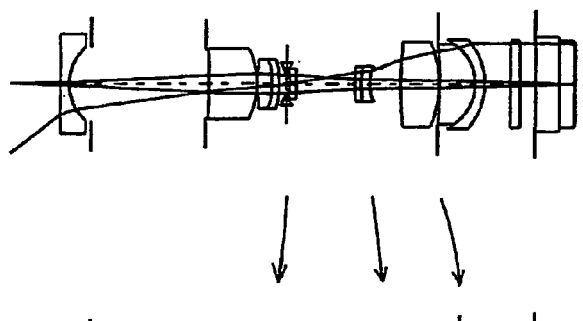
Figure 5E:
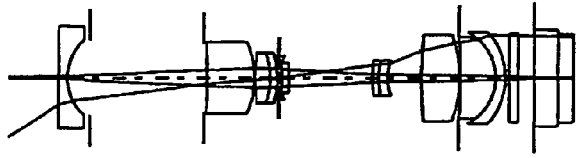

FIG. 5(a) illustrates the objective lens at the wide-angle end and at a far end defined by a working distance of 15 mm; FIG. 5(b) illustrates the objective lens at the wide-angle and in an intermediate working distance of 2.5 mm; FIG. 5(c) illustrates the objective lens at the wide-angle end and at a near end defined by a working distance of 1.58 mm; FIG. 5(d) illustrates the objective lens at a near end defined by a working distance of 1.58 mm and in the intermediate setting; and FIG. 5(e) illustrates the objective lens at a near end defined by a working distance of 1.58 mm and at the telephoto end. At the near end, the first group G1 remains fixed from the wide-angle end to the telephoto end. Meanwhile, the first subgroup G21 in the second group G2 moves monotonously to the object side and the second subgroup G22 moves monotonously to the image side, and the third group G3 moves monotonously to the image side with an increasing spacing between it and the second subgroup G22 in the second group G2 (FIGS. 5(c) to 5(e)).

Upon changing of the working distance at the wide-angle end from the far end to the near end, the second subgroup G22 in the second group G2 moves to the image side (FIGS. 5(a) to 5(c)).

Figure 16A:
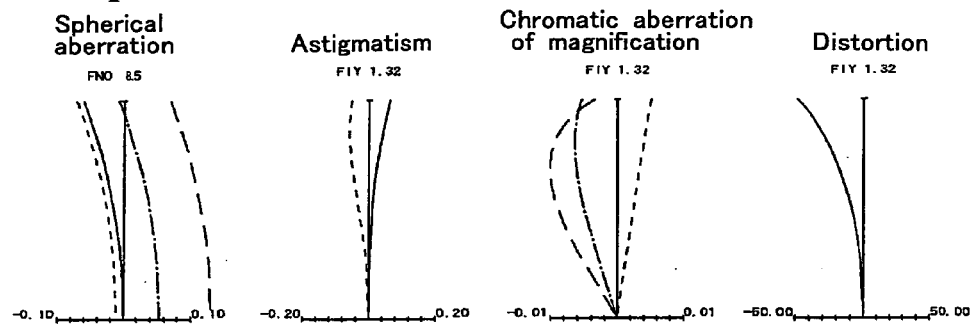
FIG. 16 is similar aberration diagrams for Example 5 as in FIG. 14.
Figure 16B:
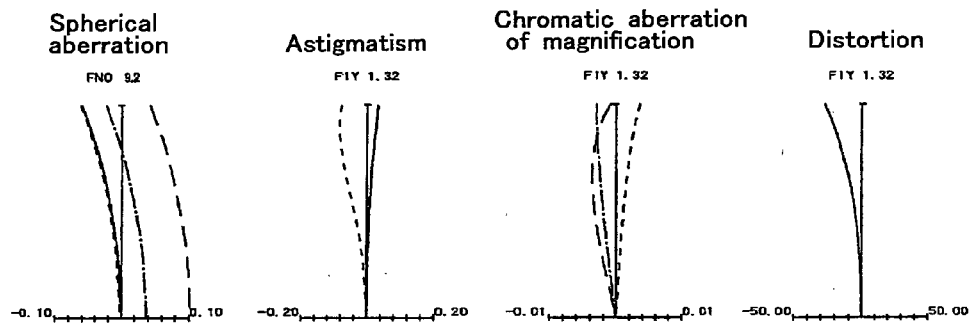
Figure 16C:
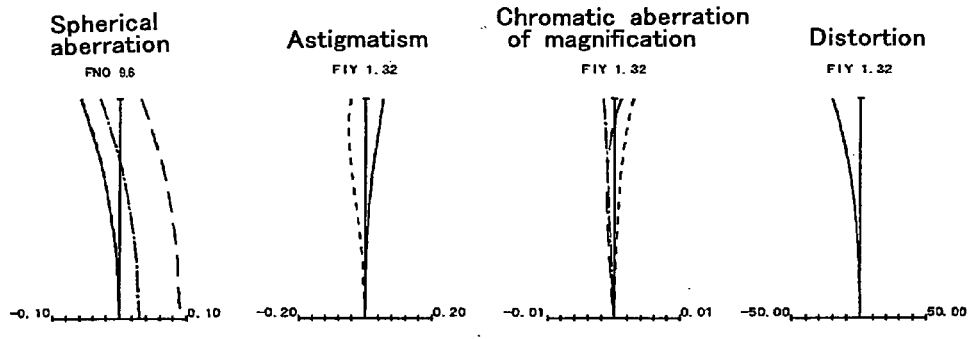
Figure 17:
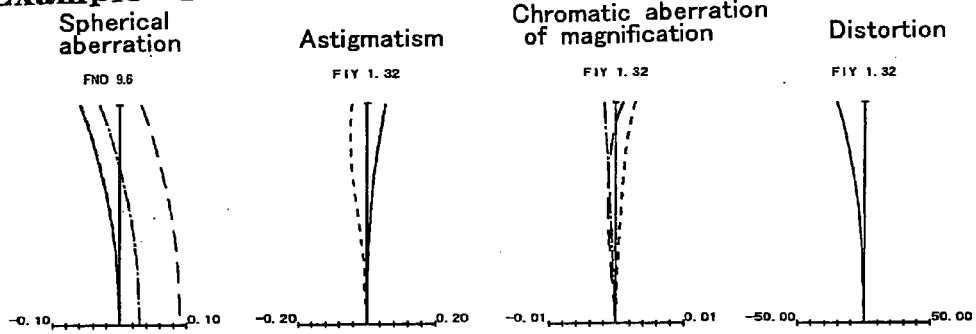
FIG. 17 is similar aberration diagrams for Example 5 as in FIG. 15.
Figure 17:
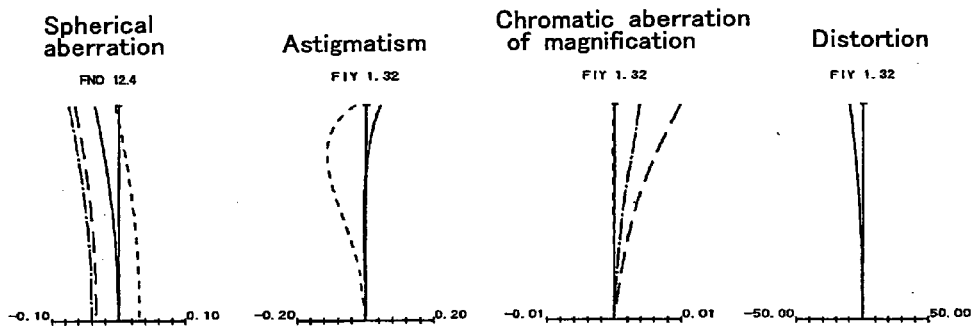
Figure 17:
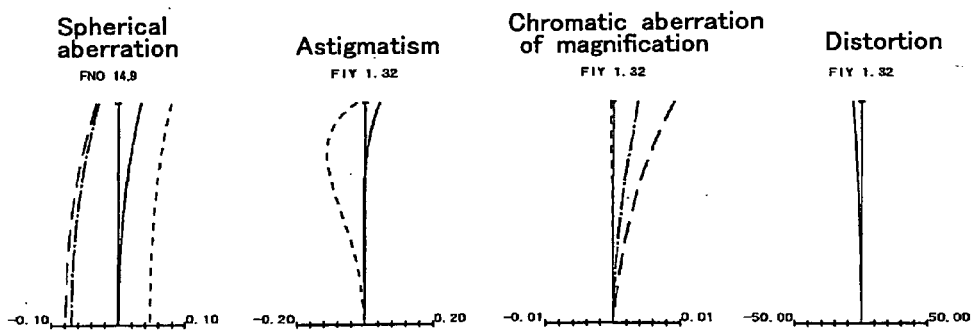

Aberration curve diagrams for Example 5 in the states of FIGS. 5(a), 5(b) and 5(c) are attached hereto as FIGS. 16(a), 16(b) and 16(c), and aberration curve diagrams in the states of FIGS. 5(c); 5(d) and 5(e) are attached hereto as FIGS. 17(a), 17(b) and 17(c).

FIG. 6 is illustrative in lens section, as in FIG. 4, of the objective lens for endoscopes according to Example 6. The first, second and third groups of this objective lens are indicated by G1, G2 and G3, respectively, and the first and second subgroups in the second group G2 are indicated by G21 and G22, respectively.

As shown in FIG. 6, the objective lens for endoscopes according to Example 6 is built up of the positive first group G1 made up of a plano-concave negative lens, a positive meniscus lens concave on its object side and a cemented lens of a double-convex positive lens and a negative meniscus lens concave on its object side, the negative second group G2 having the aperture stop S located in it and made up of a double-convex positive lens and a cemented lens of a double-concave negative lens and a positive meniscus lens convex on its object side and the positive third group G3 made up of a double-convex positive lens and a cemented lens of a double-convex positive lens and a negative meniscus lens concave on its object side. The double-convex positive lens in the second group G2 defines the positive first subgroup G21 and the cemented lens defines the negative second subgroup G22. The aperture stop S is located at the vertex position of the lens surface on the most object side of the cemented lens. The optical member P such as a laser cut filter is located on the image side of the third group G3. To the image-side optical member P in the third group G3, the cover glass C and CCD chip sealing glass D are joined, and the image plane I is positioned behind the CCD chip sealing glass D. The planes indicated by Surface Nos. 3, 4, 5, 11, 19, 20 and 26 in the numeral data given later are flare stops F.

Figure 6A:
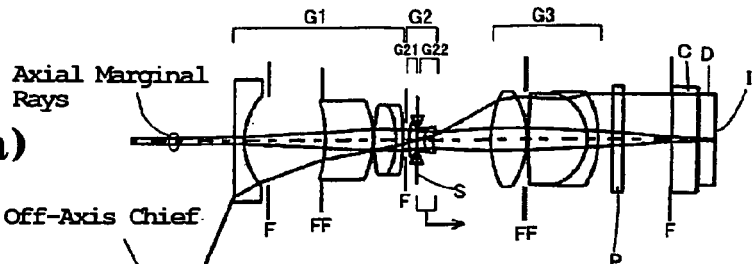
FIG. 6 is illustrative in lens section, as in FIG. 1, of the objective lens for endoscopes according to inventive Example 6.
Figure 6B:
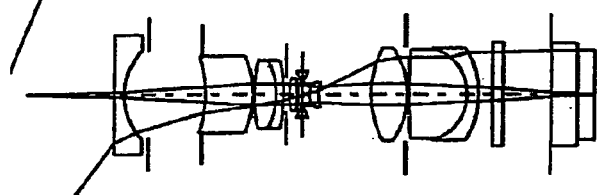
Figure 6C:
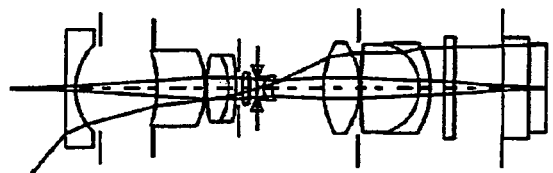
Figure 6D:
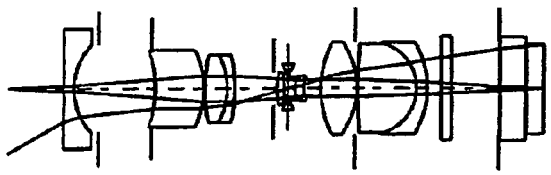
Figure 6E:
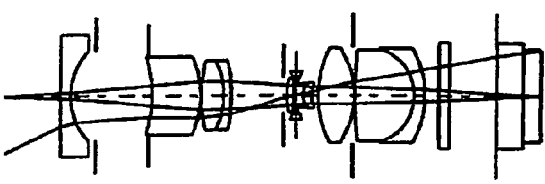

FIG. 6(a) illustrates the objective lens at the wide-angle end and at a far end defined by a working distance of 15 mm; FIG. 6(b) illustrates the objective lens at the wide-angle and in an intermediate working distance of 2.5 mm; FIG. 6(c) illustrates the objective lens at the wide-angle end and at a near end defined by a working distance of 1.58 mm; FIG. 6(d) illustrates the objective lens at the near end defined by a working distance of 1.58 mm and in the intermediate setting; and FIG. 6(e) illustrates the objective lens at a near end defined by a working distance of 1.58 mm and the telephoto end. At the near end, the first and third groups G1 and G3 remain fixed from the wide-angle end to the telephoto end. Meanwhile, the first subgroup G21 in the second group G2 moves monotonously to the image side, and the second subgroup G22 moves monotonously to the image side with a decreasing spacing between it and the first subgroup G21 (FIGS. 6(c) to 6(e)).

Upon changing of the working distance at the wide-angle end from the far end to the near end, the second subgroup G22 in the second group G2 moves to the image side (FIGS. 6(a) to 6(c)).

Figure 18A:
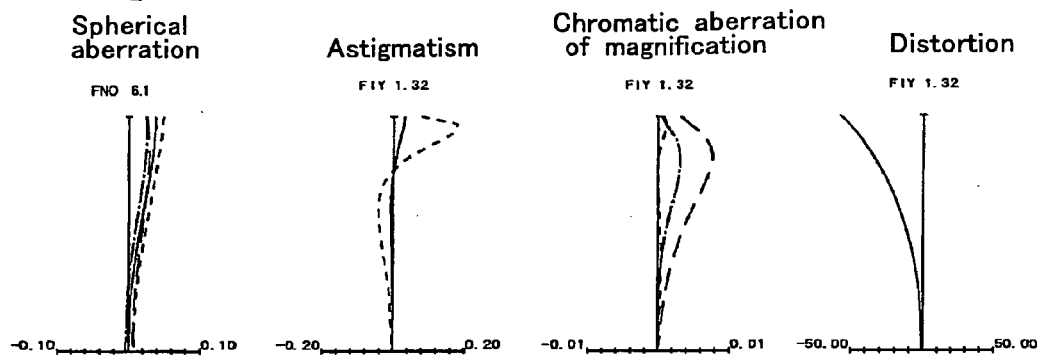
FIG. 18 is similar aberration diagrams for Example 6 as in FIG. 14.
Figure 18B:
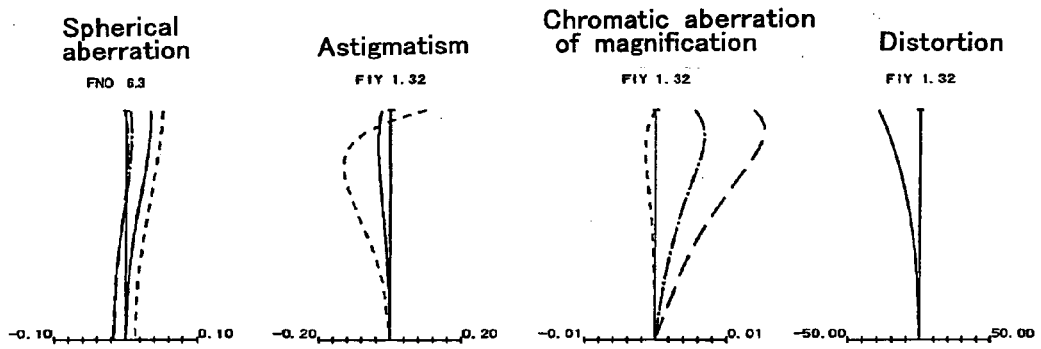
Figure 18C:
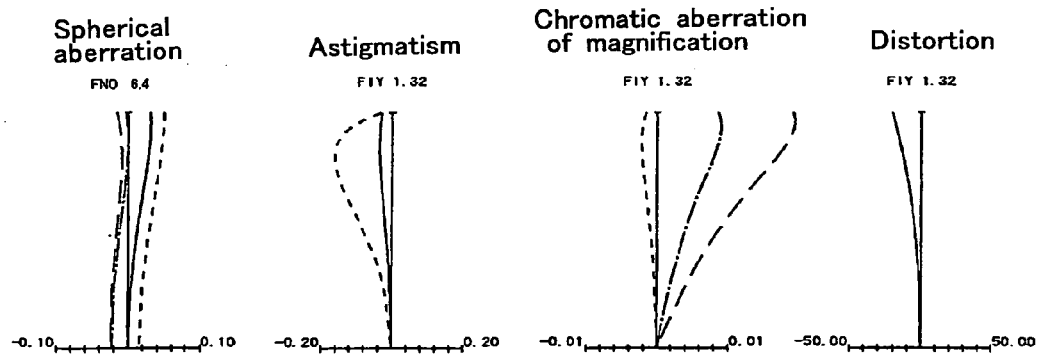
Figure 19A:
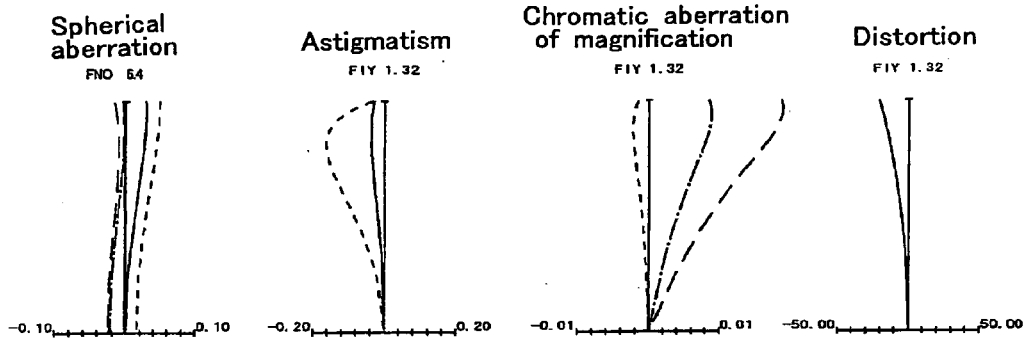
FIG. 19 is similar aberration diagrams for Example 6 as in FIG. 15.
Figure 19B:
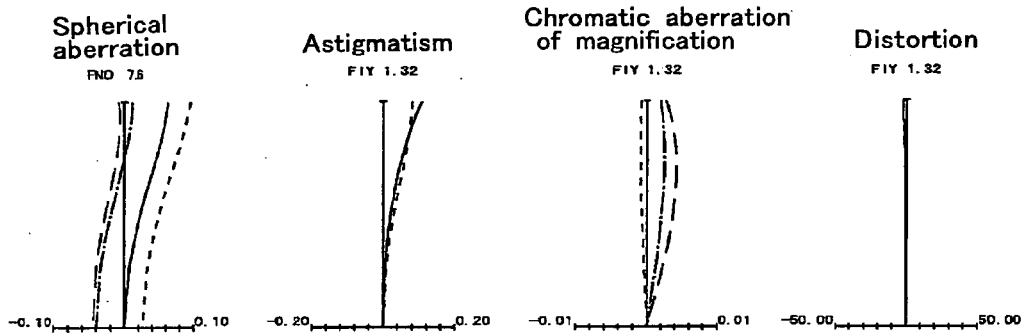
Figure 19C:
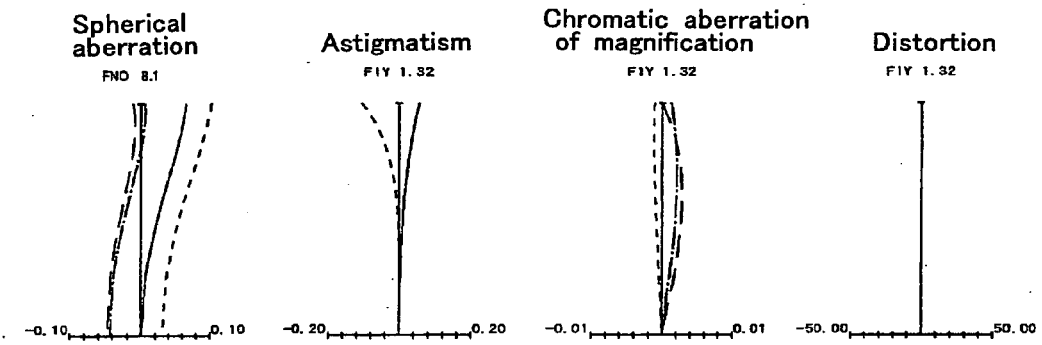

Aberration curve diagrams for Example 6 in the states of FIGS. 6(a), 6(b) and 6(c) are attached hereto as FIGS. 18(a), 18(b) and 18(c), and aberration curve diagrams in the states of FIGS. 6(c), 6(d) and 6(e) are attached hereto as FIGS. 19(a), 19(b) and 19(c).

FIG. 7 is illustrative in lens section, as in FIG. 4, of the objective lens for endoscopes according to Example 7. The first, second and third groups of this objective lens are indicated by G1, G2 and G3, respectively, and the first and second subgroups in the third group G3 are indicated by G31 and G32, respectively.

As shown in FIG. 7, the objective lens for endoscopes according to Example 7 is built up of the positive first group G1 made up of a plano-concave negative lens, a positive meniscus lens concave on its object side and a cemented lens of a double-convex positive lens and a negative meniscus lens concave on its object side, the negative second group G2 having the aperture stop S located integrally on its object side and made up of a cemented lens of a double-concave negative lens and a positive meniscus lens convex on its object side, and the positive third group G3 made up of two double-convex positive lenses and a cemented lens of a double-convex positive lens and a negative meniscus lens concave on its object side. The two double-convex positive lenses in the third group G3 define the positive first subgroup G31, and the cemented lens defines the second subgroup G32. Two optical members P such as laser cut filters are provided, one located between the plano-concave negative lens and the positive meniscus lens in the first group G1, and another on the image side of the third group G3. To the image side of the image-side optical member P in the third group G3 the cover glass C and CCD chip sealing glass D are joined. The image plane I is positioned behind the CCD chip sealing glass D. The planes indicated by Surface Nos. 3, 4, 20, 21 and 27 in the numeral data given later are flare stops F.

Figure 7A:
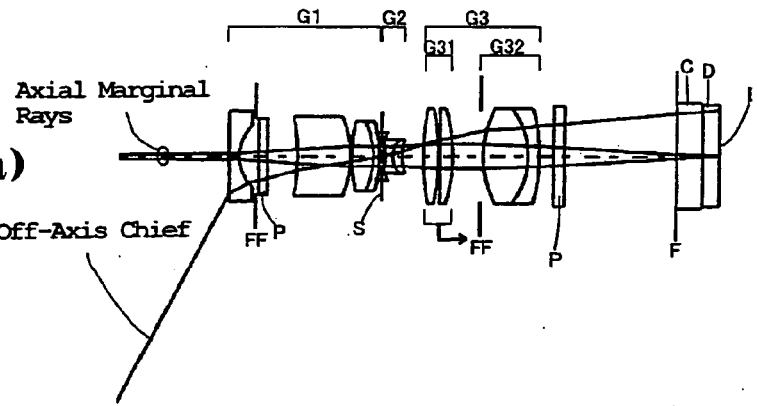
FIG. 7 is illustrative in lens section, as in FIG. 1, of the objective lens for endoscopes according to inventive Example 7.
Figure 7B:
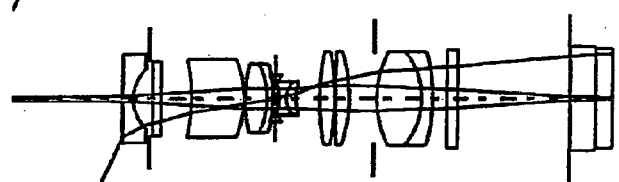
Figure 7C:
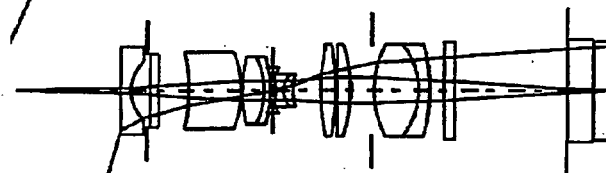
Figure 7D:
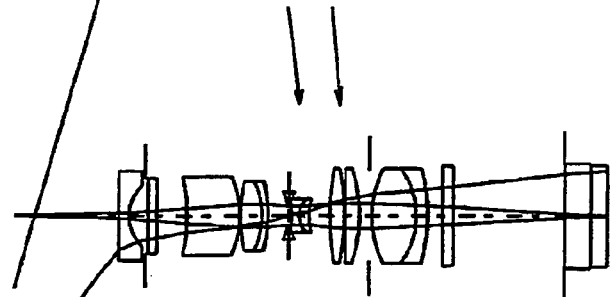
Figure 7E:
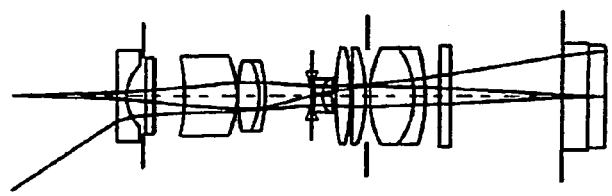

FIG. 7(a) illustrates the objective lens at the wide-angle end and at a far end defined by a working distance of 12 mm; FIG. 7(b) illustrates the objective lens at the wide-angle end and in an intermediate working distance of 6 mm; FIG. 7(c) illustrates the objective lens at the wide-angle end and at a near end defined by a working distance of 3 mm; FIG. 7(d) illustrates the objective lens at the near end defined by a working distance of 3 mm and in the intermediate setting; and FIG. 7(e) illustrates the objective lens at a near end defined by a working distance of 3 mm and at the telephoto end. At the near end the first group G1 and the second subgroup G32 in the third group G3 remain fixed from the wide-angle end to the telephoto end. Meanwhile, the second group G2 moves monotonously to the image side, and the first subgroup G31 in the third group G3 moves monotonously to the image side with a decreasing spacing between it and the second group G2 (FIGS. 7(c) to 7(e)).

Upon changing of the working distance at the wide-angle end from the far end to the near end, the first subgroup G31 in the third group G3 moves to the image side (FIGS. 7(a) to 7(c)).

Figure 20:
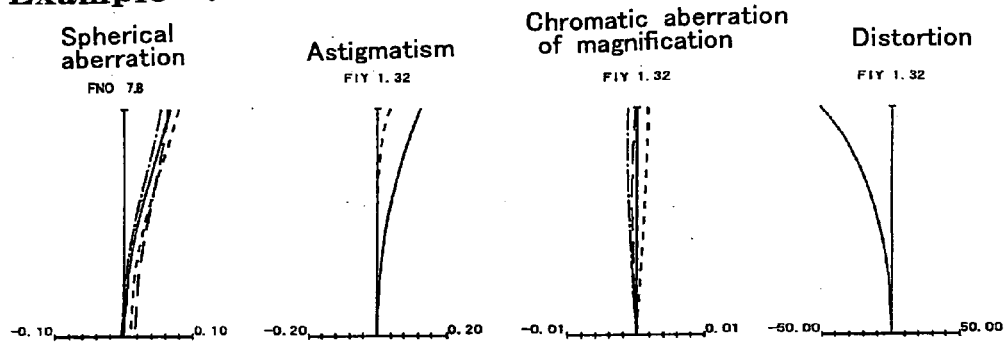
FIG. 20 is similar aberration diagrams for Example 7 as in FIG. 14.
Figure 20:
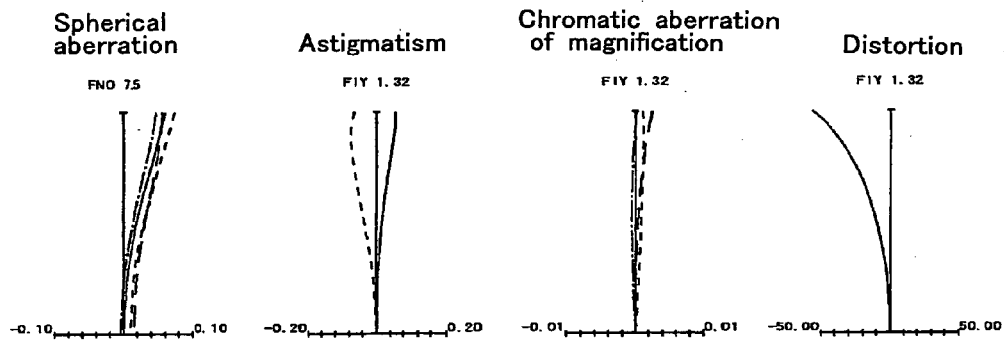
Figure 20:
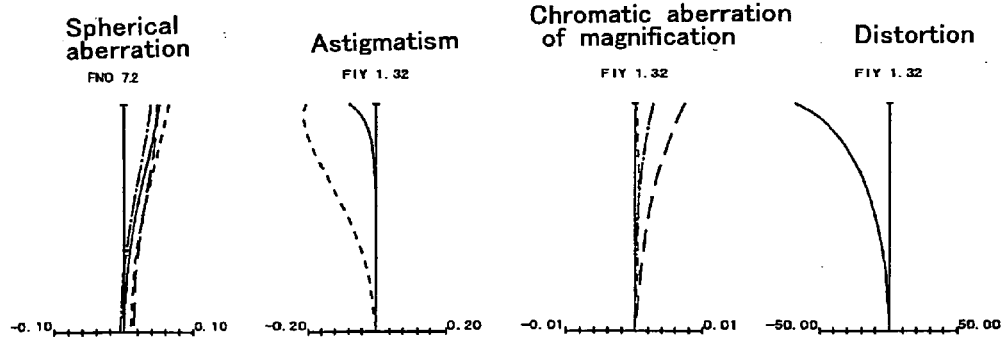
Figure 21A:
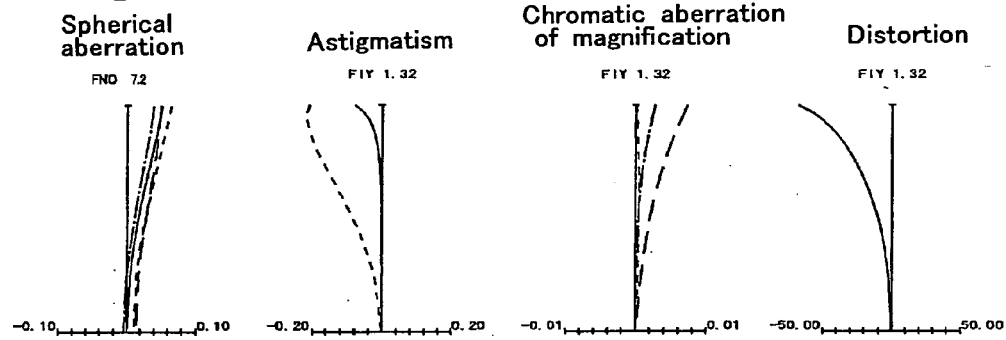
FIG. 21 is similar aberration diagrams for Example 7 as in FIG. 15.
Figure 21B:
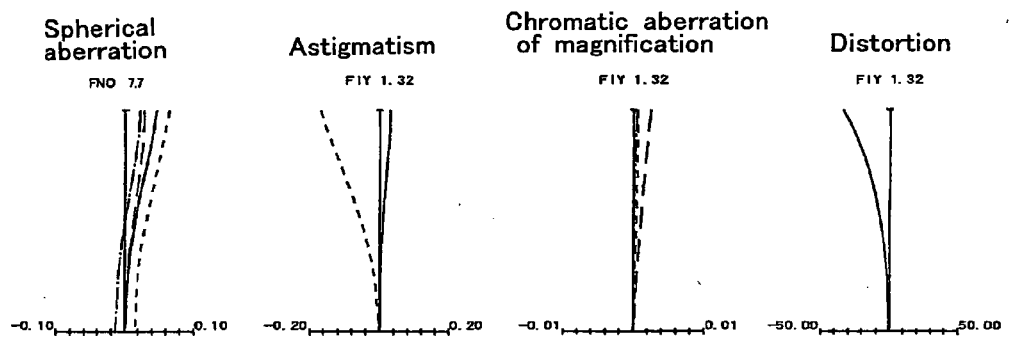
Figure 21C:
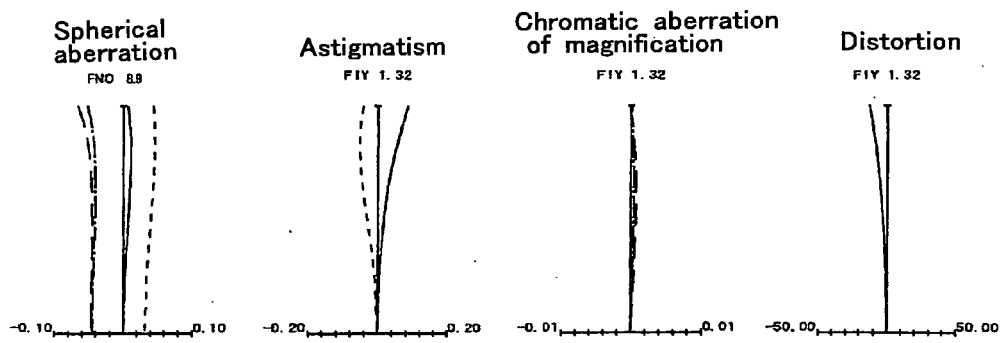

Aberration curve diagrams for Example 7 in the states of FIGS. 7(a), 7(b) and 7(c) are attached hereto as FIGS. 20(a), 20(b) and 20(c), and aberration curve diagrams in the states of FIGS. 7(c), 7(d) and 7(e) are attached hereto as FIGS. 21(a), 21(b) and 21(c).

In what follows, numeral data about Examples 1 to 7 are given. In the following tables, INF, WD, f, 2w, Fno and IH stand for infinity, the working distance, the focal length of the whole system, the angle of view (°), the effective F-number and the image height, respectively. WF means that the objective lens is at the wide-angle end and working at a far end; MF that the objective lens is in the intermediate setting and working at a far end; TF that the objective lens is at the telephoto end and working at a far end; WN that the objective lens is at the wide-angle end and working at a near end; MN that the objective lens is in the intermediate setting and working at a near end; TN that the objective lens is at the telephoto end and working at a near end; and WM that the objective lens is at the wide-angle end and working in an intermediate working distance.

EXAMPLE 1

| No | r | d | nd | vd |
|---|---|---|---|---|
| Object Plane | INF | Variable | | |
| 1 | INF | 0.3200 | 1.88300 | 40.78 |
| 2 | 1.5938 | 1.1309 | | |
| 3 | INF | 0.0300 | | |
| 4 | INF | 0.3100 | 1.51400 | 75.00 |
| 5 | INF | 0.0710 | | |
| 6 | INF | 0.1220 | | |
| 7 | 34.8300 | 0.2500 | 1.92286 | 18.90 |
| 8 | 5.4265 | 0.6336 | 1.72916 | 54.68 |
| 9 | −3.2527 | 0.0200 | | |
| 10 | INF | 0.0000 | | |
| 11 | 7.3301 | 0.3594 | 1.88300 | 40.76 |
| 12 | −5.6706 | 0.1300 | | |
| 13 | INF | Variable | | |
| 14 (Stop) | INF | 0.0156 | | |
| 15 | −2.4871 | 0.2868 | 1.92286 | 18.90 |
| 16 | −1.9298 | 0.2500 | 1.77250 | 49.60 |
| 17 | 2.7927 | 1.5434 | | |
| 18 | INF | 0.0000 | | |
| 19 | 9.1873 | 0.9769 | 1.72916 | 54.68 |
| 20 | −3.1310 | 0.4000 | 1.92286 | 18.90 |
| 21 | −3.3270 | 0.0000 | | |
| 22 | INF | Variable | | |
| 23 | 5.0011 | 1.8054 | 1.48749 | 70.23 |
| 24 | −2.5005 | 0.4000 | 1.92286 | 18.90 |
| 25 | −7.5959 | 0.0000 | | |
| 26 | INF | 1.8171 | | |
| 27 | INF | 0.0300 | | |
| 28 | INF | 0.4000 | 1.52287 | 59.89 |
| 29 | INF | 0.0300 | | |
| 30 | INF | 0.8700 | | |
| 31 | INF | 0.0300 | | |
| 32 | INF | 1.5000 | 1.51633 | 64.14 |
| 33 | INF | 0.0100 | 1.51000 | 63.00 |
| 34 | INF | 1.2300 | 1.50600 | 60.00 |
| Image Plane | INF | | | |

| No | WF | MF | TF |
|---|---|---|---|
| d0 WD | 30.00000 | 30.00000 | 30.00000 |
| d13 | 0.04000 | 0.77732 | 1.28942 |
| d17 | 1.54336 | 1.10249 | 0.29394 |
| d22 | 0.56824 | 0.27178 | 0.56824 |
| f | 1.933 | 2.650 | 3.848 |
| 2ω | 130 | 79 | 51 |
| Fno | 7.9 | 9.0 | 11.5 |

| No | WN | MN | TN |
|---|---|---|---|
| d0 WD | 15.00000 | 15.00000 | 15.00000 |
| d13 | 0.04000 | 0.77732 | 1.28942 |
| d17 | 1.62355 | 1.26906 | 0.61828 |
| d22 | 0.48805 | 0.10522 | 0.24390 |
| f | 1.863 | 2.467 | 3.374 |
| 2ω | 139 | 85 | 57 |
| Fno | 7.6 | 8.4 | 10.3 |

IH: 1.843

EXAMPLE 2

| No | r | d | nd | vd |
|---|---|---|---|---|
| Object Plane | INF | Variable | | |
| 1 | INF | 0.3200 | 1.88300 | 40.78 |
| 2 | 1.6901 | 0.5000 | | |
| 3 | INF | 0.0300 | | |
| 4 | INF | 0.3100 | 1.51400 | 75.00 |
| 5 | INF | Variable | | |
| 6 | INF | 0.0000 | | |
| 7 | −12.8991 | 0.2500 | 1.92286 | 18.90 |
| 8 | 6.3401 | 0.7526 | 1.72916 | 54.68 |
| 9 | −4.6231 | 0.0200 | | |
| 10 | INF | 0.0000 | | |
| 11 | 4.1327 | 0.5121 | 1.88300 | 40.76 |
| 12 | −4.8047 | 0.1300 | | |
| 13 | INF | Variable | | |
| 14 (Stop) | INF | 0.0156 | | |
| 15 | −2.4350 | 0.4367 | 1.92286 | 18.90 |
| 16 | −1.6442 | 0.2500 | 1.77250 | 49.60 |
| 17 | 3.2380 | Variable | | |
| 18 | INF | 0.0000 | | |
| 19 | 8.6027 | 1.0500 | 1.72916 | 54.68 |
| 20 | −3.1216 | 0.4000 | 1.92286 | 18.90 |
| 21 | −3.9692 | 0.0000 | | |
| 22 | INF | 0.6352 | | |
| 23 | 4.7756 | 1.5806 | 1.48749 | 70.23 |
| 24 | −2.9286 | 0.4000 | 1.92286 | 18.90 |
| 25 | −8.0116 | 0.0000 | | |
| 26 | INF | 2.2846 | | |
| 27 | INF | 0.0300 | | |
| 28 | INF | 0.4000 | 1.52287 | 59.89 |
| 29 | INF | 0.0300 | | |
| 30 | INF | 0.8700 | | |
| 31 | INF | 0.0300 | | |
| 32 | INF | 1.5000 | 1.51633 | 64.14 |
| 33 | INF | 0.0100 | 1.51000 | 63.00 |
| 34 | INF | 1.2300 | 1.50600 | 60.00 |
| Image Plane | INF | | | |

| No | WF | MF | TF |
|---|---|---|---|
| d0 WD | 30.00000 | 30.00000 | 30.00000 |
| d5 | 1.11528 | 0.67496 | 0.29971 |
| d13 | 0.04000 | 0.92634 | 1.90414 |
| d17 | 1.39706 | 0.95105 | 0.34850 |
| d22 | 0.63516 | 0.63516 | 0.63516 |
| f | 1.992 | 3.085 | 4.780 |
| 2ω | 130 | 68 | 40 |
| Fno | 7.5 | 8.5 | 9.8 |

| No | WN | MN | TN |
|---|---|---|---|
| d0 WD | 15.00000 | 15.00000 | 15.00000 |
| d5 | 1.11528 | 0.67496 | 0.29971 |
| d13 | 0.04000 | 0.92634 | 1.90414 |
| d17 | 1.48981 | 1.17094 | 0.88019 |
| d22 | 0.54241 | 0.41527 | 0.10347 |
| f | 1.921 | 2.842 | 4.022 |
| 2ω | 140 | 74 | 47 |
| Fno | 7.3 | 7.9 | 8.3 |

IH: 1.843

EXAMPLE 3

| No | r | d | nd | vd |
|---|---|---|---|---|
| Object Plane | INF | Variable | | |
| 1 | INF | 0.3200 | 1.88300 | 40.78 |
| 2 | 1.6074 | 0.5000 | | |
| 3 | INF | 0.0300 | | |
| 4 | INF | 0.3100 | 1.51400 | 75.00 |
| 5 | INF | Variable | | |
| 6 | INF | 0.0000 | | |
| 7 | 9.1923 | 0.2500 | 1.92286 | 18.90 |
| 8 | 2.8938 | 0.5953 | 1.72916 | 54.68 |
| 9 | −6.5967 | 0.0200 | | |

-continued

| No | r | d | nd | vd |
|---|---|---|---|---|
| 10 | INF | 0.0000 | | |
| 11 | 5.7227 | 0.4527 | 1.88300 | 40.76 |
| 12 | −3.7543 | 0.1300 | | |
| 13 | INF | Variable | | |
| 14 (Stop) | INF | 0.0156 | | |
| 15 | −2.2196 | 0.2950 | 1.92286 | 18.90 |
| 16 | −1.3591 | 0.2500 | 1.77250 | 49.60 |
| 17 | 2.5968 | Variable | | |
| 18 | INF | 0.0000 | | |
| 19 | 8.0113 | 0.8841 | 1.72916 | 54.68 |
| 20 | −3.7093 | 0.4000 | 1.92286 | 18.90 |
| 21 | −3.8534 | 0.0000 | | |
| 22 | INF | Variable | | |
| 23 | 4.8969 | 1.7048 | 1.48749 | 70.23 |
| 24 | −2.7383 | 0.4000 | 1.92286 | 18.90 |
| 25 | −10.6574 | 0.0000 | | |
| 26 | INF | 2.3299 | | |
| 27 | INF | 0.0300 | | |
| 28 | INF | 0.4000 | 1.52287 | 59.89 |
| 29 | INF | 0.0300 | | |
| 30 | INF | 0.8700 | | |
| 31 | INF | 0.0300 | | |
| 32 | INF | 1.5000 | 1.51633 | 64.14 |
| 33 | INF | 0.0100 | 1.51000 | 63.00 |
| 34 | INF | 1.2300 | 1.50600 | 60.00 |
| Image Plane | INF | | | |

| No | WF | MF | TF |
|---|---|---|---|
| d0 WD | 30.00000 | 30.00000 | 30.00000 |
| d5 | 1.33832 | 0.44745 | 0.35239 |
| d13 | 0.04000 | 1.18004 | 1.90142 |
| d17 | 1.76980 | 1.62838 | 0.29711 |
| d22 | 0.45710 | 0.34936 | 1.05430 |
| f | 2.004 | 3.464 | 6.007 |
| 2ω | 130 | 60 | 30 |
| Fno | 6.9 | 7.2 | 10.7 |

| No | WN | MN | TN |
|---|---|---|---|
| d0 WD | 15.00000 | 15.00000 | 15.00000 |
| d5 | 1.33832 | 0.44745 | 0.35239 |
| d13 | 0.04000 | 1.18004 | 1.90142 |
| d17 | 1.86369 | 1.91436 | 1.04408 |
| d22 | 0.36321 | 0.06337 | 0.30734 |
| f | 1.926 | 3.109 | 4.748 |
| 2ω | 140 | 67 | 37 |
| Fno | 6.7 | 6.5 | 8.5 |

IH: 1.843

EXAMPLE 4

| No | r | d | nd | vd |
|---|---|---|---|---|
| Object Plane | INF | Variable | | |
| 1 | INF | 0.2852 | 1.88300 | 40.78 |
| 2 | 1.3795 | 0.3703 | | |
| 3 | INF | 0.4520 | | |
| 4 | −2.0035 | 1.2220 | 1.51742 | 52.43 |
| 5 | −1.8638 | Variable | | |
| 6 | 3.5818 | 0.8886 | 1.77250 | 49.60 |
| 7 | −2.2796 | 0.2251 | 1.92286 | 18.90 |
| 8 | −4.3562 | Variable | | |
| 9 (Stop) | INF | 0.1000 | | |
| 10 | 7.2143 | 0.2101 | 1.48749 | 70.23 |
| 11 | 1.0214 | 0.2626 | 1.59270 | 35.31 |
| 12 | 1.2569 | Variable | | |
| 13 | 2.4586 | 0.7623 | 1.48749 | 70.23 |
| 14 | −9.5466 | −0.0600 | | |
| 15 | INF | 0.0225 | | |
| 16 | INF | 0.0675 | | |
| 17 | 7.9078 | 1.1519 | 1.48749 | 70.23 |
| 18 | −1.7384 | 0.3152 | 1.92286 | 18.90 |
| 19 | −3.5738 | 0.4052 | | |
| 20 | INF | 0.3002 | 1.52287 | 59.89 |
| 21 | INF | 0.5103 | | |
| 22 | INF | 0.0225 | | |
| 23 | INF | 0.7504 | 1.51633 | 64.14 |
| 24 | INF | 0.0075 | 1.51000 | 63.00 |
| 25 | INF | 0.4878 | 1.50600 | 60.00 |
| Image Plane | INF | | | |

| No | WF | WM | WN |
|---|---|---|---|
| d0 WD | 15.00000 | 5.00000 | 2.47641 |
| d5 | 2.37084 | 2.37084 | 2.37084 |
| d8 | 0.23811 | 0.41902 | 0.63584 |
| d12 | 1.35379 | 1.17288 | 0.95606 |
| f | 1.293 | 1.319 | 1.342 |
| 2ω | 133 | 123 | 112 |
| Fno | 6.5 | 6.5 | 6.5 |

| No | WN | MN | TN |
|---|---|---|---|
| d0 WD | 2.47641 | 2.47641 | 2.47641 |
| d5 | 2.37084 | 2.18400 | 0.59660 |
| d8 | 0.63584 | 0.72341 | 1.93630 |
| d12 | 0.95606 | 1.06587 | 1.47100 |
| f | 1.342 | 1.403 | 2.246 |
| 2ω | 112 | 107 | 57 |
| Fno | 6.5 | 6.5 | 6.5 |

IH: 1.32

EXAMPLE 5

| No | r | d | nd | vd |
|---|---|---|---|---|
| Object Plane | INF | Variable | | |
| 1 | INF | 0.2852 | 1.88300 | 40.78 |
| 2 | 1.6075 | 0.7238 | | |
| 3 | INF | 3.6139 | | |
| 4 | INF | 0.0225 | | |
| 5 | INF | 0.0976 | | |
| 6 | −26.3995 | 1.5408 | 1.51742 | 52.43 |
| 7 | −2.4896 | 0.0225 | | |
| 8 | 9.0371 | 0.4669 | 1.77250 | 49.60 |
| 9 | −2.1986 | 0.2251 | 1.92286 | 18.90 |
| 10 | −3.2664 | Variable | | |
| 11 (Stop) | INF | 0.1000 | | |
| 12 | −2.2086 | 0.2000 | 1.48749 | 70.23 |
| 13 | −8.2251 | Variable | | |
| 14 | 13.8916 | 0.2000 | 1.48749 | 70.23 |
| 15 | 3.6020 | 0.2626 | 1.59270 | 35.31 |
| 16 | 1.3361 | Variable | | |
| 17 | 18.6833 | 1.2110 | 1.48749 | 70.23 |
| 18 | −3.6664 | −0.0600 | | |
| 19 | INF | 0.0225 | | |
| 20 | INF | 0.0675 | | |
| 21 | −13.0957 | 1.1256 | 1.48749 | 70.23 |
| 22 | −1.6264 | 0.3152 | 1.92286 | 18.90 |
| 23 | −2.1774 | Variable | | |
| 24 | INF | 0.3002 | 1.52287 | 59.89 |
| 25 | INF | 0.5103 | | |
| 26 | INF | 0.0225 | | |
| 27 | INF | 0.7504 | 1.51633 | 64.14 |
| 28 | INF | 0.0075 | 1.51000 | 63.00 |
| 29 | INF | 0.4878 | 1.50600 | 60.00 |
| Image Plane | INF | | | |

| No | WF | WM | WN |
|---|---|---|---|
| d0 WD | 15.00000 | 2.50000 | 1.58000 |
| d10 | 0.39846 | 0.39846 | 0.39846 |
| d13 | 0.03753 | 0.30840 | 0.42343 |
| d16 | 0.72523 | 0.45435 | 0.33933 |
| d23 | 2.74545 | 2.74545 | 2.74545 |
| f | 1.482 | 1.552 | 1.575 |
| 2ω | 22 | 104 | 98 |

-continued

| No | WN | MN | TN |
|---|---|---|---|
| d0 WD | 1.58000 | 1.58000 | 1.58000 |
| d10 | 0.39846 | 0.21892 | 0.05761 |
| d13 | 0.42343 | 1.87772 | 2.67128 |
| d16 | 0.33933 | 0.98592 | 1.08876 |
| d23 | 2.74545 | 0.82384 | 0.11018 |
| f | 1.575 | 2.035 | 2.368 |
| 2ω | 98 | 76 | 67 |
| Fno | 9.6 | 12.4 | 14.9 |

IH: 1.32

EXAMPLE 6

| No | r | d | nd | vd |
|---|---|---|---|---|
| Object Plane | INF | Variable | | |
| 1 | INF | 0.2852 | 1.88300 | 40.78 |
| 2 | 1.9184 | 0.7238 | | |
| 3 | INF | 1.5437 | | |
| 4 | INF | 0.0225 | | |
| 5 | INF | 0.0976 | | |
| 6 | −3.7117 | 1.3911 | 1.51742 | 52.43 |
| 7 | −2.8978 | 0.0225 | | |
| 8 | 4.4284 | 0.6206 | 1.77250 | 49.60 |
| 9 | −2.3756 | 0.2251 | 1.92286 | 18.90 |
| 10 | −4.7641 | Variable | | |
| 11 | INF | 0.1000 | | |
| 12 | 2.7474 | 0.2000 | 1.48749 | 70.23 |
| 13 | −4.8446 | Variable | | |
| 14 (Stop) | −1.5664 | 0.2000 | 1.48749 | 70.23 |
| 15 | 0.5046 | 0.2626 | 1.59270 | 35.31 |
| 16 | 0.8956 | Variable | | |
| 17 | 2.9923 | 1.0656 | 1.48749 | 70.23 |
| 18 | −2.5355 | −0.0600 | | |
| 19 | INF | 0.0225 | | |
| 20 | INF | 0.0675 | | |
| 21 | 14.3330 | 1.7134 | 1.48749 | 70.23 |
| 22 | −1.4362 | 0.3152 | 1.92286 | 18.90 |
| 23 | −2.7938 | 0.4052 | | |
| 24 | INF | 0.3002 | 1.52287 | 59.89 |
| 25 | INF | 1.3696 | | |
| 26 | INF | 0.0225 | | |
| 27 | INF | 0.7504 | 1.51633 | 64.14 |
| 28 | INF | 0.0075 | 1.51000 | 63.00 |
| 29 | INF | 0.4878 | 1.50600 | 60.00 |
| Image Plane | INF | | | |

| No | WF | WM | WN |
|---|---|---|---|
| d0 WD | 15.00000 | 2.50000 | 1.58000 |
| d10 | 0.07990 | 0.07990 | 0.07990 |
| d13 | 0.01999 | 0.15965 | 0.21836 |
| d16 | 1.65870 | 1.51904 | 1.46032 |
| f | 1.340 | 1.471 | 1.525 |
| 2ω | 136 | 111 | 103 |
| Fno | 6.1 | 6.3 | 6.4 |

| No | WN | MN | TN |
|---|---|---|---|
| d0 WD | 1.58000 | 1.58000 | 1.58000 |
| d10 | 0.07990 | 1.12790 | 1.52252 |
| d13 | 0.21836 | 0.11901 | 0.05762 |
| d16 | 1.46032 | 0.50059 | 0.18081 |
| f | 1.525 | 1.956 | 2.069 |
| 2ω | 103 | 62 | 53 |
| Fno | 6.4 | 7.6 | 8.1 |

IH: 1.32

EXAMPLE 7

| No | r | d | nd | vd |
|---|---|---|---|---|
| Object Plane | INF | Variable | | |
| 1 | INF | 0.2852 | 1.88300 | 40.78 |
| 2 | 1.2030 | 0.4728 | | |
| 3 | INF | 0.0225 | | |
| 4 | INF | 0.0750 | | |
| 5 | INF | 0.2326 | 1.51400 | 75.00 |
| 6 | INF | 0.8549 | | |
| 7 | −5.3784 | 1.4735 | 1.51742 | 52.43 |
| 8 | −3.0051 | 0.0225 | | |
| 9 | 4.2923 | 0.6159 | 1.77250 | 49.60 |
| 10 | −2.4224 | 0.1724 | 1.92286 | 18.90 |
| 11 | −4.0625 | Variable | | |
| 12 (Stop) | INF | 0.1000 | | |
| 13 | −1.7601 | 0.2101 | 1.48749 | 70.23 |
| 14 | 0.7295 | 0.2626 | 1.59270 | 35.31 |
| 15 | 1.5143 | Variable | | |
| 16 | 7.6234 | 0.4342 | 1.49700 | 81.54 |
| 17 | −6.6885 | 0.0292 | | |
| 18 | 316.6520 | 0.4015 | 1.61700 | 62.80 |
| 19 | −4.4302 | Variable | | |
| 20 | INF | 0.0225 | | |
| 21 | INF | 0.0675 | | |
| 22 | 3.0885 | 1.2813 | 1.48749 | 70.23 |
| 23 | −2.3179 | 0.3152 | 1.92286 | 18.90 |
| 24 | −5.2265 | 0.4052 | | |
| 25 | INF | 0.3002 | 1.52287 | 59.89 |
| 26 | INF | 3.1250 | | |
| 27 | INF | 0.0225 | | |
| 28 | INF | 0.7504 | 1.51633 | 64.14 |
| 29 | INF | 0.0075 | 1.51000 | 63.00 |
| 30 | INF | 0.4878 | 1.50600 | 60.00 |
| Image Plane | INF | | | |

| No | WF | WM | WN |
|---|---|---|---|
| d0 WD | 12.00000 | 6.00000 | 3.00000 |
| d11 | 0.06789 | 0.06789 | 0.06789 |
| d15 | 0.60929 | 0.68679 | 0.80266 |
| d19 | 0.78399 | 0.70649 | 0.59062 |
| f | 1.480 | 1.423 | 1.344 |
| 2ω | 125 | 132 | 149 |
| Fno | 7.8 | 7.5 | 7.2 |

| No | WN | MN | TN |
|---|---|---|---|
| d0 WD | 3.00000 | 3.00000 | 3.00000 |
| d11 | 0.06789 | 0.58785 | 1.32180 |
| d15 | 0.80266 | 0.60020 | 0.12000 |
| d19 | 0.59062 | 0.27314 | 0.02519 |
| f | 1.344 | 1.568 | 2.011 |
| 2ω | 149 | 105 | 67 |
| Fno | 7.2 | 7.7 | 8.9 |

IH: 1.32

Tabulated below are the values of the conditions and the values of the condition elements in Examples 1 to 7.

|  | Examples | | | | | | |
|---|---|---|---|---|---|---|---|
|  | 1 | 2 | 3 | 4 | 5 | 6 | 7 |
| 2ω | 130 | 130 | 130 | 133 | 122 | 136 | 125 |
| (1) | 0.646 | 0.936 | 0.929 | 1.006 | −0.230 | 1.077 | 0.847 |
| (2) | 0.041 | 0.046 | 0.047 | 0.308 | 0.260 | 0.148 | 0.131 |
| (3) | 1.096 | 0.768 | 1.424 | 0.184 | 0.885 | 0.319 | 0.634 |
| (4) | −0.479 | −0.416 | −0.531 | 0.060 | −0.182 | −0.355 | −0.136 |
| fw | 1.933 | 1.992 | 2.004 | 1.293 | 1.482 | 1.340 | 1.480 |
| ra | 1.594 | 1.690 | 1.607 | 1.380 | 1.608 | 1.918 | 1.203 |
| rb | 34.830 | −12.899 | 9.192 | −2.004 | −26.400 | −3.712 | −5.378 |
| D12w | 0.040 | 0.040 | 0.040 | 0.636 | 0.398 | 0.080 | 0.068 |
| D12t | 1.289 | 1.904 | 1.901 | 1.936 | 0.058 | 1.523 | 1.322 |
| ΔDwd | 0.080 | 0.092 | 0.094 | 0.398 | 0.386 | 0.198 | 0.193 |
| βwd | −2.087 | −2.404 | −1.885 | 16.641 | −5.491 | −2.817 | −7.345 |

While Example 5 does not satisfy Condition (1), it is to be understood that the second subgroup G22 that bears a substantial part of the zooming function has moved to the image side: the spacing between the positive first group and the negative second group substantially grows wide from the wide-angle side to the telephoto side. By calculation, (D12$t$–D12$w$) indicative of the amount of movement of the second subgroup G22 is found to be 1.89, and Condition (1) is found to be 1.89/fw=1.89/1.478=1.28, indicating that the inventive idea is fully embraced.

The inventive objective lens for endoscopes, as described above, may be embodied as follows.

[1] An objective lens for endoscopes, characterized by having an angle of view of 100° or greater at a wide-angle end, and comprising, in order from an object side thereof, a positive first group, a negative second group and a positive third lens group, wherein:

the third comprises a positive first (3-1) subgroup and a positive second (3-2) subgroup, a lens subgroup in at least the second group moves to (1) bring about a change in a focal length of a whole system and (2) correct an image position for movement in association with a focal length change, and one subgroup in the second group and the third group moves to an image side from a longer working distance (WD) side toward a shorter working distance side to (3) correct a focal position for movement in association with a working distance change.

[2] The objective lens for endoscopes according to [1], characterized in that the second group has an aperture stop.

[3] The objective lens for endoscopes according to [1], characterized by satisfying the following conditions (1), (2), (3) and (4):

$$0.4 < (D12t - D12w)/fw < 1.4 \quad (1)$$

$$0.02 < \Delta Dwd/fw < 0.4 \quad (2)$$

$$0 < (rb+ra)/(rb-ra) < 2 \quad (3)$$

$$-0.7 < 1/\beta wd < 0.2 \quad (4)$$

where fw is a focal length of a whole system at the wide-angle end, a figure being obtained in a far end-defining working distance;

D12$w$ is a spacing between the first group and the second group at the wide-angle end;

D12$t$ is a spacing between the first group and the second group at the telephoto end;

ΔDwd is an amount of movement of a moving group upon changing of the working distance from a far end to a near end, provided that a plus sign is indicative of a direction of movement of the moving group to an image side;

ra is a radius of curvature of an image-side surface of a first lens in the first group;

rb is s radius of curvature of an object-side surface of a second lens in the first group; and βwd is an imaging magnification of the moving group upon a working distance change, a figure being obtained at the wide-angle end in a far end-defining working distance.

[5] The objective lens for endoscopes according to any one of [1] to [4], characterized in that after ordinary far viewing, the working distance is changed from a longer side to a shorter side for near viewing, and then the focal length of the whole system is changed while the working distance remains fixed for near viewing to implement magnified viewing with higher magnifications.

[6] The objective lens for endoscopes according to any one of [1] to [4], characterized in that:

the second group moves to the image side from a wide-angle side toward a telephoto side, the first (3-1) subgroup in the third group moves in an orbit distinct from that of the second group in such a way as to correct the image position for movement in association with a focal length change, and the first (3-1) subgroup moves to the image side from a longer side toward a shorter side of the working distance (WD).

[7] The objective lens for endoscopes according to any one of [1] to [4], characterized in that:

the first group comprises a negative first (1-1) subgroup and a positive second (1-2) subgroup, the second group moves to the image side from a wide-angle side to a telephoto side, the second (1-2) subgroup in the second group moves in an orbit distinct from that of the second group in such a way as to correct the image position for movement in association with a focal length change, and the first (3-1) subgroup moves to the image side from a longer side toward a shorter side of the working distance (WD).

[8] The objective lens for endoscopes according to any one of [1] to [4], characterized in that:

the first group comprises a negative first (1-1) subgroup and a positive second (1-2) subgroup, from a wide-angle side to a telephoto side, the second (1-2) subgroup moves to the object side and the second group moves to the image side, the first (3-1) subgroup moves in an orbit distinct from those of the second (1-2) subgroup and the second group in such a way as to correct the image position for movement in association with a focal length change, and the first (3-1) subgroup moves to the image side from a longer side toward a shorter side of the working distance (WD).

[9] The objective lens for endoscopes according to any one of [1] to [4], characterized in that:

the first group comprises a negative first (1-1) subgroup and a positive second (1-2) subgroup, the second (1-2) subgroup moves to the object side from a wide-angle side to a telephoto side, the second group moves in an orbit distinct from that of the second (1-2) subgroup in such a way as to correct the image position for movement in association with a focal length change, and the second group moves to the image side from a longer side toward a shorter side of the working distance (WD).

[10] The objective lens for endoscopes according to any one of [1], [2] and [4], characterized in that:

the second group comprises a negative first (2-1) subgroup and a negative second (2-2) subgroup, from a wide-angle side to a telephoto side, the first (2-1) subgroup moves to the object side and the second (2-2) subgroup moves to the image side, the third group moves in an orbit distinct from those of the first (2-1) subgroup and the second (2-2) subgroup in such a way as to correct the image position for movement in association with a focal length change, and the second (2-2) subgroup moves to the image side from a longer side toward a shorter side of the working distance (WD).

[11] The objective lens for endoscopes according to any one of [1] to [4], characterized in that:

the second group comprises a positive first (2-1) subgroup and a negative second (2-2) subgroup, the second (2-2) subgroup moves to the image side from a wide-angle side to a telephoto side, the first (2-1) subgroup moves in an orbit distinct from that of the second (2-2) subgroup in such a way as to correct the image position for movement in association with a focal length change, and the second (2-2) subgroup moves to the image side from a longer side toward a shorter side of the working distance (WD).

INDUSTRIAL APPLICABILITY

According to the present invention, there can be an objective lens for endoscopes provided which is well compatible with endoscopes and has independently a zooming function and a focusing function for magnified viewing.

EXPLANATION OF THE REFERENCES

G1: $1^{st}$ group
G2: $2^{nd}$ group
G3: $3^{rd}$ group
G11: the first (1-1) subgroup in the $1^{st}$ group
G12: the second (1-2) subgroup in the $1^{st}$ group
G21: the first (2-1) subgroup in the $2^{nd}$ group
G22: the second (2-2) subgroup in the $2^{nd}$ group
G31: the first (3-1) subgroup in the $3^{rd}$ group
G32: the second (3-2) subgroup in the $3^{rd}$ group
S: Aperture Stop
I: Image Plane
P: Optical Members (such as laser cut filters, infrared cut filters or Optical Low-Pass Filters)
C: Cover Glass
D: CCD Chip Sealing Glass
F: Flare Stop

What is claimed is:

1. A zoom objective lens for endoscopes, characterized by having an angle of view (2ω) of 100° or greater at a wide-angle end, and comprising, in order from an object side thereof, a positive first group, a negative second group and a positive third lens group, wherein:

said third group comprises a positive first (3-1) subgroup and a positive second (3-2) subgroup, the second group comprises subgroups, wherein a lens subgroup in at least said second group moves to (1) bring about a change in a focal length of a whole system and (2) correct an image position for movement in association with a focal length change, and one subgroup in said second group and said third group moves to an image side from a longer working distance (WD) side being a far end toward a shorter working distance side being a near end to correct a focal position for movement in association with a working distance change, and wherein said zoom objective lens for endoscopes satisfies the following conditions:

$$0.4 < (D12t - D12w)/fw \leq 1.077 \quad (1)'$$

$$0.02 < \Delta Dwd/fw < 0.4 \quad (2)$$

$$0 < (rb + ra)/(rb - ra) < 2 \quad (3)$$

$$-0.7 < 1/\beta wd < 0.2 \quad (4)$$

where fw is a focal length of a whole system at the wide-angle end, a figure being obtained in a far end-defining working distance;

D12w is a spacing between the first group and the second group at the wide-angle end;

D12t is a spacing between the first group and the second group at a telephoto end;

ΔDwd is an amount of movement of a moving group upon changing of the working distance from a far end to a near end, provided that a plus sign is indicative of a direction of movement of the moving group to an image side;

ra is a radius of curvature of an image-side surface of a first lens in the first group;

rb is s radius of curvature of an object-side surface of a second lens in the first group; and βwd is an imaging magnification of the moving group upon a working distance change, a figure being obtained at the wide-angle end in a far end-defining working distance.

2. A zoom objective lens for endoscopes, characterized by having an angle of view (2ω) of 100° or greater at a wide-angle end, and comprising, in order from an object side thereof, a positive first group, a negative second group and a positive third lens group, wherein:

the second group has an aperture stop, the third group comprises a positive first (3-1) subgroup and a positive second (3-2) subgroup, the second group comprises subgroups, wherein a lens subgroup in at least said second group moves to (1) bring about a change in a focal length of a whole system and (2) correct an image position for movement in association with a focal length change, and one subgroup in the second group and the third group moves to an image side from a longer working distance (WD) side being a far end toward a shorter working distance side being a near end to correct a focal position for movement in association with a working distance change, and wherein said zoom objective lens for endoscopes satisfies the following conditions:

$$0.4 < (D12t - D12w)/fw \leq 1.077 \quad (1)'$$

$$0.02 < \Delta Dwd/fw < 0.4 \quad (2)$$

$$0 < (rb+ra)/(rb-ra) < 2 \quad (3)$$

$$-0.7 < 1/\beta wd < 0.2 \quad (4)$$

where fw is a focal length of a whole system at the wide-angle end, a figure being obtained in a far end-defining working distance;

D12w is a spacing between the first group and the second group at the wide-angle end;

D12t is a spacing between the first group and the second group at the telephoto end;

ΔDwd is an amount of movement of a moving group upon changing of the working distance from a far end to a near end, provided that a plus sign is indicative of a direction of movement of the moving group to an image side;

ra is a radius of curvature of an image-side surface of a first lens in the first group;

rb is s radius of curvature of an object-side surface of a second lens in the first group; and βwd is an imaging magnification of the moving group upon a working distance change, a figure being obtained at the wide-angle end in a far end-defining working distance.

3. The zoom objective lens for endoscopes according to any one of claims 1 and 2, characterized in that after ordinary far viewing, the working distance is changed from a longer side to a shorter side for near viewing, and then the focal length of the whole system is changed while the working distance remains fixed for near viewing to implement magnified viewing with higher magnifications.

4. The zoom objective lens for endoscopes according to any one of claims 1 and 2, characterized in that:
the second group moves to the image side from a wide-angle side to a telephoto side,
the first (3-1) subgroup of the third group moves in an orbit distinct from that of the second group in such a way as to correct the image position for movement in association with a focal length change, and
the first (3-1) subgroup of the third group moves to the image side from a longer side to a shorter side of the working distance (WD).

5. The zoom objective lens for endoscopes according to any one of claims 1 and 2, characterized in that:
the first group comprises a negative first (1-1) subgroup and a positive second (1-2) subgroup,
the second group moves to the image side from a wide-angle side to a telephoto side,
the second (1-2) subgroup of the first group moves in an orbit distinct from that of the second group in such a way as to correct the image position for movement in association with a focal length change, and
the first (3-1) subgroup of the third group moves to the image side from a longer side to a shorter side of the working distance (WD).

6. The zoom objective lens for endoscopes according to any one of claims 1 and 2, characterized in that:
the first group comprises a negative first (1-1) subgroup and a positive second (1-2) subgroup,
from a wide-angle side to a telephoto side, the second (1-2) subgroup of the first group moves to the object side and the second group moves to the image side,
the first (3-1) subgroup of the third group moves in an orbit distinct from those of the second (1-2) subgroup of the first group and the second group in such a way as to correct the image position for movement in association with a focal length change, and
the first (3-1) subgroup of the third group moves to the image side from a longer side to a shorter side of the working distance (WD).

7. The zoom objective lens for endoscopes according to any one of claims 1 and 2, characterized in that:
the first group comprises a negative first (1-1) subgroup and a positive second (1-2) subgroup,
the second (1-2) subgroup of the first group moves to the object side from a wide-angle side to a telephoto side,
the second group moves in an orbit distinct from that of the second (1-2) subgroup of the first group in such a way as to correct the image position for movement in association with a focal length change, and
the second group moves to the image side from a longer side to a shorter side of the working distance (WD).

8. The zoom objective lens for endoscopes according to any one of claims 1 and 2, characterized in that:
the second group comprises a negative first (2-1) subgroup and a negative second (2-2) subgroup,
from a wide-angle side to a telephoto side, the first (2-1) subgroup of the second group moves to the object side and the second (2-2) subgroup of the second group moves to the image side,
the third group moves in an orbit distinct from those of the first (2-1) subgroup of the second group and the second (2-2) subgroup of the second group in such a way as to correct the image position for movement in association with a focal length change, and
the second (2-2) subgroup of the second group moves to the image side from a longer side to a shorter side of the working distance (WD).

9. The zoom objective lens for endoscopes according to any one of claims 1 and 2, characterized in that:
the second group comprises a positive first (2-1) subgroup and a negative second (2-2) subgroup,
the second (2-2) subgroup of the second group moves to the image side from a wide-angle side to a telephoto side,
the first (2-1) subgroup of the second group moves in an orbit distinct from that of the second (2-2) subgroup of the second group in such a way as to correct the image position for movement in association with a focal length change, and
the second (2-2) subgroup of the second group moves to the image side from a longer side to a shorter side of the working distance (WD).

* * * * *